United States Patent
Presswood et al.

(10) Patent No.: US 7,412,298 B2
(45) Date of Patent: Aug. 12, 2008

(54) METHOD AND SYSTEM FOR MORPHOMETRIC ANALYSIS OF HUMAN DENTAL OCCLUSAL FUNCTION AND USES THEREOF

(76) Inventors: Ronald G. Presswood, 513 Ripple Creek, Houston, TX (US) 77024; Ronald G. Presswood, Jr., 807 Saybrook W., Houston, TX (US) 77024-4505

(*) Notice: Subject to any disclaimer, the term of this patent is extended or adjusted under 35 U.S.C. 154(b) by 0 days.

(21) Appl. No.: 10/592,042

(22) PCT Filed: Feb. 14, 2004

(86) PCT No.: PCT/US2005/004465

§ 371 (c)(1),
(2), (4) Date: Feb. 14, 2007

(87) PCT Pub. No.: WO2005/079699

PCT Pub. Date: Sep. 1, 2005

(65) Prior Publication Data

US 2007/0168073 A1 Jul. 19, 2007

Related U.S. Application Data

(60) Provisional application No. 60/544,725, filed on Feb. 13, 2004.

(51) Int. Cl.
*G06F 19/00* (2006.01)
(52) U.S. Cl. .................................. 700/118; 700/98
(58) Field of Classification Search ................ 700/245, 700/251, 118, 97; 703/2
See application file for complete search history.

(56) References Cited

U.S. PATENT DOCUMENTS

| | | | |
|---|---|---|---|
| 5,798,924 A * | 8/1998 | Eufinger et al. | 700/117 |
| 6,238,601 B1 * | 5/2001 | Salomonson et al. | 264/16 |
| 2002/0119423 A1 * | 8/2002 | Chishti et al. | 433/213 |

FOREIGN PATENT DOCUMENTS

EP 0 910997 A2 * 4/1999

* cited by examiner

*Primary Examiner*—Kidest Bahta
(74) *Attorney, Agent, or Firm*—Robert W Strozier

(57) ABSTRACT

A method is disclosed for determining and predicting temporomandibular joint (TMJ) motion and to use the predictive model to prepare improved TMJ replacement joints, improved crown, cap or bridge contouring, improved teeth alignments and placements, and improved mouth guard and dentures.

12 Claims, 35 Drawing Sheets

Mathematical Suppositions

- Jaw motion about the pivot TMJ is constrained by wear surface on two specific teeth

Mathematical Suppositions

- Geometry is defined by position vectors and normal vectors

Mathematical Suppositions
- The jaw rigid body motion is defined by a rotation about a directional vector at the pivot TMJ
*Euler's Theorem: the most general displacement of a rigid body with one point fixed is a rotation about some axis.*
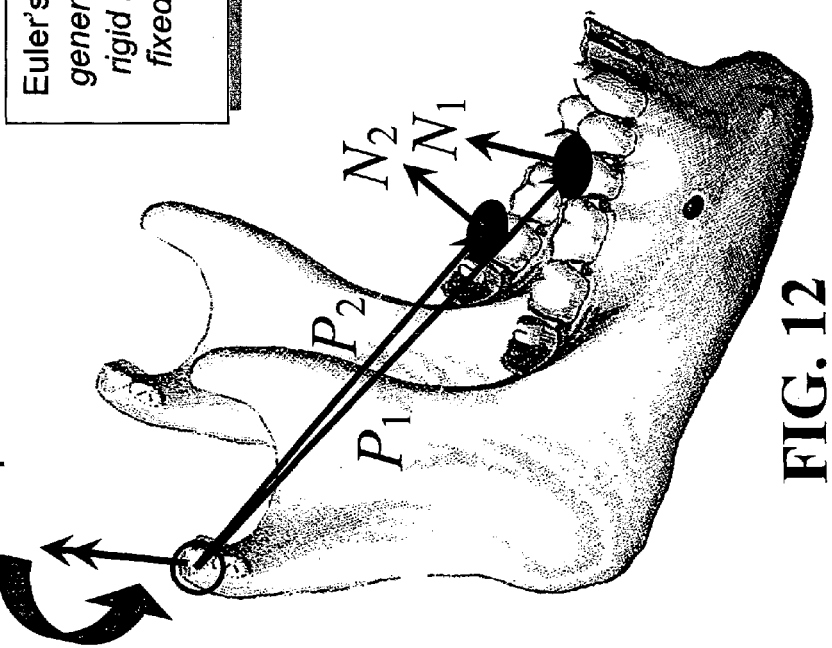
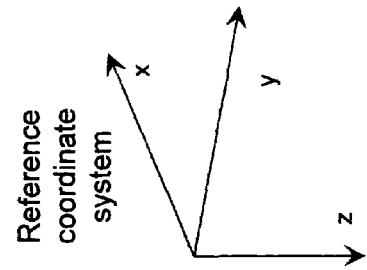
Reference coordinate system
FIG. 12

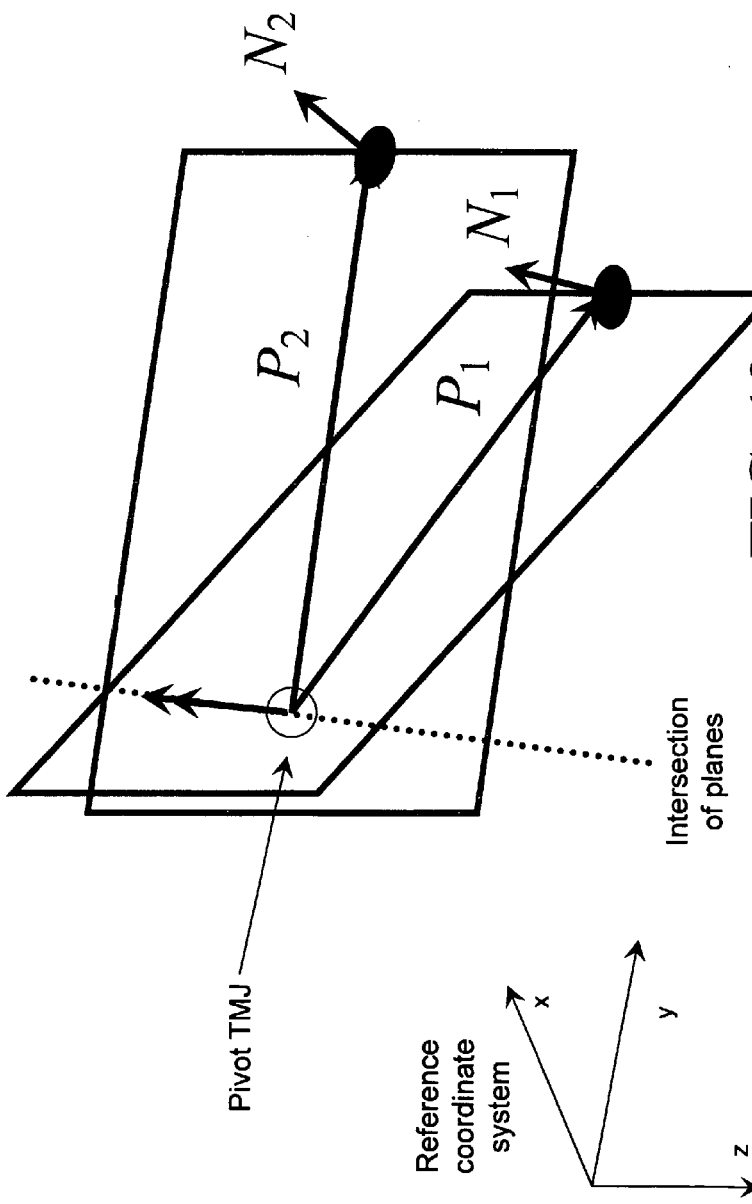

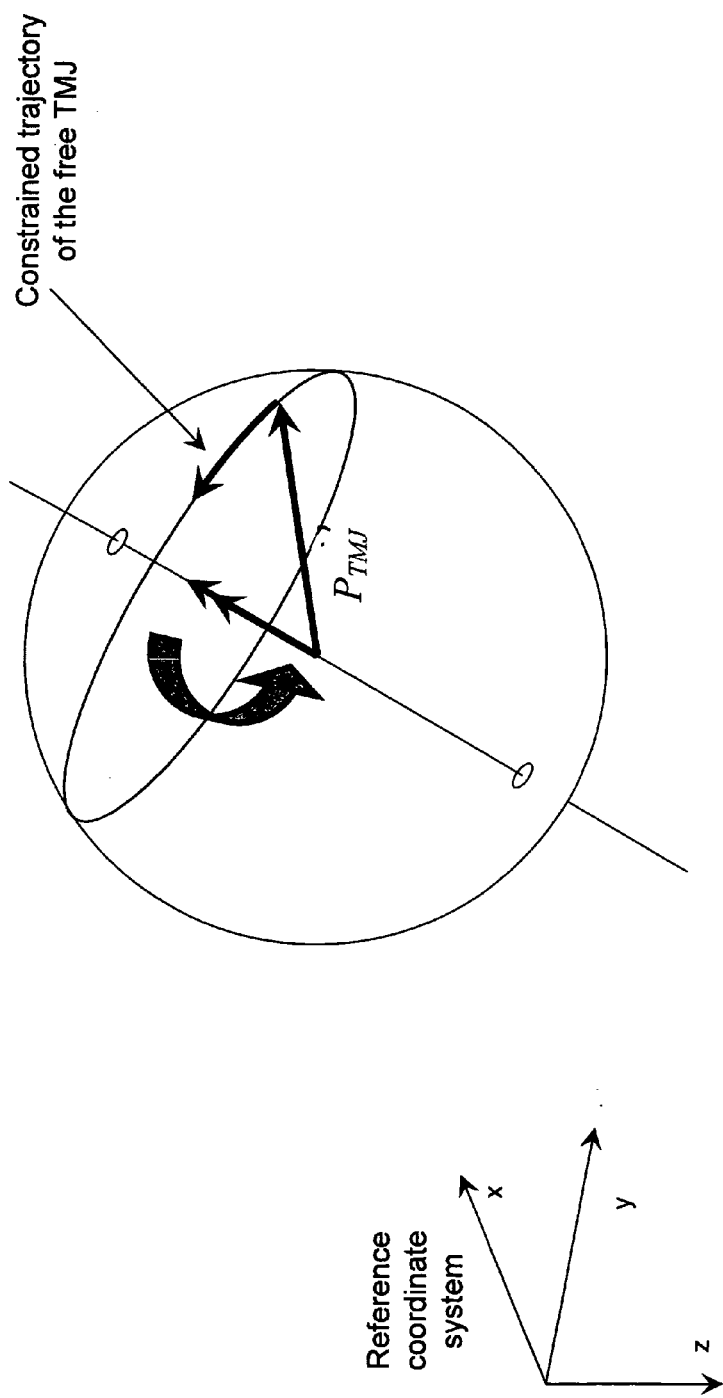

Mathematical Solution
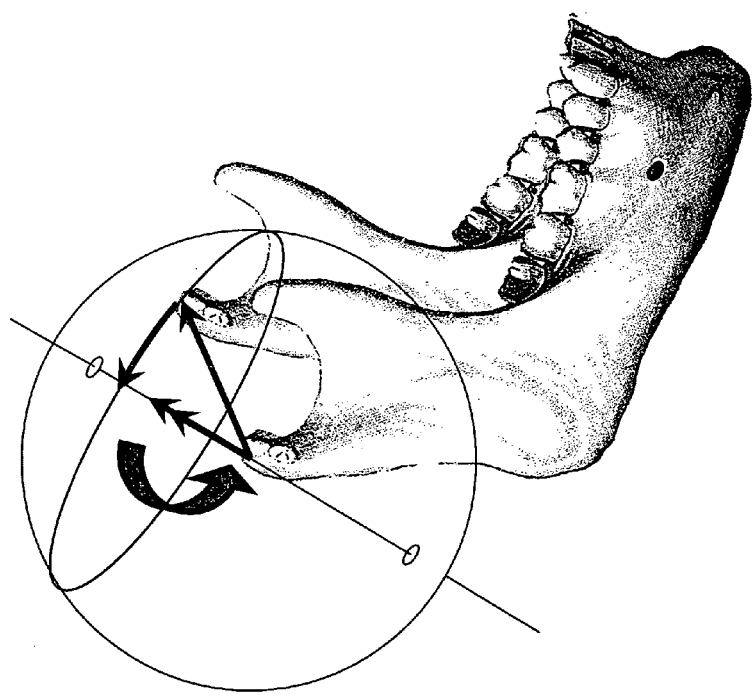
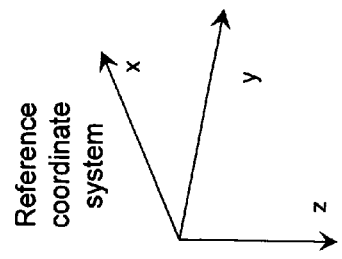
Reference coordinate system
FIG. 14B

Skull Sample A10

| A10 | Plane Position | | |
|---|---|---|---|
| | X | Y | Z |
| RMTJ LL | -37.30205 | -27.73642 | -772.99151 |
| T2 LL | -24.01224 | 8.43019 | -723.62974 |
| T12 LL | 24.56079 | 27.97058 | -716.37889 |
| LTMJ RL | 38.47396 | -29.58010 | -767.99221 |
| T15 RL | 29.53961 | 3.17493 | -723.75534 |
| T5 RL | -15.95057 | 31.64806 | -715.48246 |

X and Y coordinate sign change to maintain consistency with A4 skull

| A10 | Normal Vector | | |
|---|---|---|---|
| | X | Y | Z |
| RMTJ LL | -0.66888 | -0.62674 | 0.39974 |
| T2 LL | -0.28217 | -0.41450 | 0.86520 |
| T12 LL | -0.67285 | -0.18045 | 0.71743 |
| LTMJ RL | 0.53208 | -0.39467 | 0.74909 |
| T15 RL | 0.30654 | -0.52001 | 0.79726 |
| T5 RL | 0.38435 | -0.47885 | 0.78929 |

Skull Sample A12

TMJ and Tooth Locations

| A12 | Plane Position | | |
|---|---|---|---|
| | X | Y | Z |
| RMTJ LL | -55.51980 | -40.29024 | -732.62374 |
| T3 LL | -25.45141 | 19.81153 | -699.28100 |
| T11 LL | 13.19534 | 38.34905 | -701.68756 |
| LTMJ RL | 38.33101 | -37.73624 | -739.27025 |
| T16 RL | 22.21094 | -0.96218 | -703.21902 |
| T4 RL | -22.27687 | 26.07841 | -700.84245 |

| A12 | Normal Vector | | |
|---|---|---|---|
| | X | Y | Z |
| RMTJ LL | 0.04540 | -0.64929 | 0.75919 |
| T3 LL | 0.02275 | 0.44860 | 0.89344 |
| T11 LL | -0.58631 | 0.09613 | 0.80436 |
| LTMJ RL | 0.34482 | -0.76162 | 0.54867 |
| T16 RL | 0.46746 | -0.07938 | 0.88045 |
| T4 RL | 0.50952 | -0.02144 | 0.86019 |

Skull Sample A14

| A14 | Plane Position | | |
|---|---|---|---|
| | X | Y | Z |
| RMTJ LL | -46.87120 | -36.46056 | -807.03142 |
| T2 LL | -31.71687 | 17.22490 | -794.33224 |
| T6 LL | 11.07834 | 44.56431 | -800.91019 |
| LTMJ RL | 35.63926 | -35.57592 | -807.84101 |
| T16 RL | 22.10209 | 6.28197 | -790.27852 |
| T5 RL | -24.86349 | 39.31903 | -798.80090 |

| A14 | Normal Vector | | |
|---|---|---|---|
| | X | Y | Z |
| RMTJ LL | -0.61464 | 0.13055 | 0.77793 |
| T2 LL | -0.27369 | 0.17450 | 0.94586 |
| T6 LL | 0.70267 | -0.32606 | -0.63241 |
| LTMJ RL | 0.36918 | 0.14208 | 0.91843 |
| T16 RL | 0.43915 | 0.01397 | 0.89831 |
| T5 RL | 0.43369 | 0.39731 | 0.80874 |

Skull Sample A

Plane Position

| A | X | Y | Z |
|---|---|---|---|
| RMTJ LL | -41.09687 | -21.37327 | -925.88466 |
| T2 LL | -33.27735 | 13.32836 | -874.89271 |
| T11 LL | 10.13802 | 41.59843 | -860.82557 |
| LTMJ RL | 36.94236 | -21.48514 | -921.30952 |
| T15 RL | 17.62691 | 8.68860 | -871.68761 |
| T6 RL | -22.99831 | 44.93133 | -862.66019 |

X and Y coordinate sign change to maintain consistency with A4 skull

Normal Vector

| A | X | Y | Z |
|---|---|---|---|
| RMTJ LL | -0.83145 | -0.54582 | 0.10377 |
| T2 LL | -0.82317 | -0.21873 | 0.52398 |
| T11 LL | -0.66204 | -0.08313 | 0.74485 |
| LTMJ RL | 0.37258 | -0.62756 | 0.68363 |
| T15 RL | 0.30889 | -0.57239 | 0.75958 |
| T6 RL | 0.27309 | -0.04056 | 0.96113 |

TMJ and Tooth Locations

Skull Sample cl3

| cl3 | Plane Position | | |
|---|---|---|---|
| | X | Y | Z |
| RMTJ LL | -32.30478 | -38.59284 | -719.82094 |
| T2 LL | -20.65164 | 7.16208 | -701.36878 |
| T10 LL | 10.81801 | 43.67405 | -719.20736 |
| LTMJ RL | 41.08782 | -35.81332 | -722.52551 |
| T15 RL | 21.31764 | 11.52634 | -702.83011 |
| T7 RL | -15.49997 | 41.25363 | -718.98353 |

| cl3 | Normal Vector | | |
|---|---|---|---|
| | X | Y | Z |
| RMTJ LL | -0.62242 | 0.18799 | 0.75977 |
| T2 LL | 0.00569 | 0.36626 | 0.93050 |
| T10 LL | 0.17827 | 0.72401 | 0.66635 |
| LTMJ RL | 0.16923 | -0.23790 | 0.95643 |
| T15 RL | 0.15606 | 0.53613 | 0.82959 |
| T7 RL | -0.02103 | 0.57601 | 0.81717 |

Skull Sample cl3

| cl3 | Plane Position | | |
|---|---|---|---|
| | X | Y | Z |
| RMTJ LL | -32.30478 | -38.59284 | -719.82094 |
| T2 LL | -20.65164 | 7.16208 | -701.36878 |
| T10 LL | 10.81801 | 43.67405 | -719.20736 |
| LTMJ RL | 41.08782 | -35.81332 | -722.52551 |
| T15 RL | 21.31764 | 11.52634 | -702.83011 |
| T7 RL | -15.49997 | 41.25363 | -718.98353 |

| cl3 | Normal Vector | | |
|---|---|---|---|
| | X | Y | Z |
| RMTJ LL | -0.62242 | 0.18799 | 0.75977 |
| T2 LL | 0.00569 | 0.36626 | 0.93050 |
| T10 LL | 0.17827 | 0.72401 | 0.66635 |
| LTMJ RL | 0.16923 | -0.23790 | 0.95643 |
| T15 RL | 0.15606 | 0.53613 | 0.82959 |
| T7 RL | -0.02103 | 0.57601 | 0.81717 |

View Parallel TMJ Trajectory

- Multiple possibilities of surface orientations exists between the TMJ and the Mandibular Cavity

Mandibular Cavity Normal Vector Correlation

| | | Adjusted Measured | | | Analytical Model | | | Angle Error |
|---|---|---|---|---|---|---|---|---|
| | | X | Y | Z | X | Y | Z | |
| A4 | Left | -0.788 | 0.613 | 0.061 | -0.983 | 0.092 | 0.160 | 32.8 |
| | Right | 0.902 | 0.406 | -0.151 | 0.998 | -0.061 | -0.018 | 28.7 |
| A10 | Left | -0.920 | 0.351 | -0.175 | -0.920 | -0.194 | 0.341 | 1.2 |
| | Right | 0.883 | 0.445 | -0.148 | 0.912 | 0.281 | -0.299 | 12.9 |
| A12 | Left | -0.001 | 0.999 | 0.053 | -0.863 | -0.045 | 0.504 | 91.0 |
| | Right | 0.578 | 0.780 | -0.24 | 0.821 | 0.126 | -0.557 | 45.0 |
| A14 | Left | -0.001 | -0.999 | -0.043 | -0.927 | -0.026 | 0.375 | 89.4 |
| | Right | 0.757 | -0.166 | -0.632 | 0.79 | 0.125 | -0.600 | 17.0 |

FIG. 25A

Mandibular Cavity Normal Vector Correlation

| | | Adjusted Measured | | | Analytical Model | | | Angle Error |
|---|---|---|---|---|---|---|---|---|
| | | X | Y | Z | X | Y | Z | |
| A | Left | -0.961 | -0.275 | -0.002 | -0.98 | -0.168 | 0.110 | 9.0 |
| | Right | 0.798 | 0.587 | -0.134 | 0.822 | 0.489 | -0.293 | 10.8 |
| Anat | Left | -0.075 | 0.925 | -0.373 | -0.766 | 0.233 | 0.599 | 87.2 |
| | Right | -0.514 | -0.682 | 0.521 | 0.595 | 0.255 | -0.762 | 151.2 |
| cl3 | Left | -0.354 | 0.846 | -0.398 | -0.996 | -0.076 | -0.050 | 72.0 |
| | Right | 0.89 | 0.383 | -0.248 | 0.998 | 0.063 | -0.004 | 24.1 |

FIG. 25B

METHOD AND SYSTEM FOR MORPHOMETRIC ANALYSIS OF HUMAN DENTAL OCCLUSAL FUNCTION AND USES THEREOF

RELATED APPLICATIONS

This application is a 35 U.S.C.§371 nationalization of PCT/US05/04465 filed 14 Feb. 2005, which claims priority to United States Provisional Patent Application Ser. No. 60/544,725 filed 13 Feb. 2004.

BACKGROUND OF THE INVENTION

1. Field of the Invention

The present invention relates to a system and a method for determining a guide plane of a temporomandibular joint (TMJ) in an animal including a human and using the guide plane to design dental prostheses, to aid in dental reconstruction surgery, to aid in orthodontic configurations and final teeth placement, to aid in cap design and contouring and to aid in the design of mouth guards to protect and properly align the jaw.

More particularly, the present invention relates to a system and a method for determining a guide plane of an TMJ in an animal including a human and using the guide plane to design dental prostheses, to aid in dental reconstruction surgery, to aid in orthodontic configurations and final teeth placement, to aid in cap design and contouring and to the design of mouth guards to protect and properly align the jaw, where the system includes obtaining digital images at a fixed focal length of a lower and upper jaw, scanning the digital image into 3-D images, transporting the 3-D images to a 3-D software program, using a derived mathematical function and determining contact planes of functional teeth surfaces (wear facets) and a glenoid fossa, Zola's tubercle. The invention also relates to methods for using the determined teeth data to design prosthesis, to design caps, to design mouth guards, to improve orthodontic configuration to produce improved teeth alignment, to augment teeth placement to relieve stress on the TM joint.

2. Description of the Related Art

Analysis of human skulls is a delicate and difficult process. Much of the significant work that has been done in this area of study, morphometrics, has been conducted using analog techniques, i.e., direct measurements, using instrument such as calipers, dividers, rulers, grids and/or custom designed "guides".

To better understand the functional relationship of dental occlusions and the bony morphology of the skull and mandible, direct measurement and/or analog models were insufficient at supplying necessary mathematical formula to develop a predictive model evidencing the relationship.

After determining that classical analysis using analog models and protocols derived thereform did not yield the desired mathematical described relationship, the inventors sought a more detailed measurements analytical approach. First, the inventors studied radiographic techniques and attempted correlation the radiographic data to photographic evidence. However, the distortional aspect of the radiograph data rendered such techniques useless. The inventors also attempted using 3-D, corrected CT Scan data, but this technique proved difficult to manage Thus, there is a need in the art for an improved method for determining the motion of the temporomandibular joint allowing for improved dental, medical and rehabilitative prostheses, mouth guards, teeth alignment, engaging surface contouring and other similar methods.

SUMMARY OF THE INVENTION

The present invention provides a method for analyzing jaw motion including the steps of determining planes associated with wear surfaces of at least two teeth on a lower jaw, at least one of the teeth located on an ipsilateral posterior side of the jaw and at least another one of the teeth located on a contralateral anterior side of the jaw, calculating normals vectors to the two planes directed from the planes towards the upper jaw, determining position vectors between a gliding temporomandibular joint (TMJ) pivot point and a center point of each of the planes and a rotating temporomandibular joint (TMJ) pivot point.

The present invention also provides a method implemented on a computer for predicting motion of a temporomandibular joint including the steps of generating a 3-D image of an upper jaw, a lower jaw, upper and lower teeth and the temporomandibular joint (TMJ). After the image is created, a right or left TMJ pivot point is located and planar wear surfaces are determined for at least two teeth on the lower and upper jaw, at least one of the teeth located on an ipsilateral posterior side of the jaw and at least another one of the teeth located on a contralateral anterior side of the jaw. Once the pivot point and the planes are located, normal vectors to the planes directed towards the upper jaw are determined and pointing vectors are determine between the pivot point and an opposite side TMJ pivot and between the pivot point and the two normal vectors. With the vectors determined, creating a TMJ trajectory given by equation (1):

$$\begin{Bmatrix} P'_{TMJx} \\ P'_{TMJy} \\ P'_{TMJz} \end{Bmatrix} = \begin{bmatrix} \cos\Phi + E_{Rx}^2(1-\cos\Phi) & E_{Rx}E_{Ry}(1-\cos\Phi) + E_{Rz}\sin\Phi & E_{Rx}E_{Rz}(1-\cos\Phi) - E_{Ry}\sin\Phi \\ E_{Rx}E_{Ry}(1-\cos\Phi) - E_{Rz}\sin\Phi & \cos\Phi + E_{Ry}^2(1-\cos\Phi) & E_{Ry}E_{Rz}(1-\cos\Phi) + E_{Rx}\sin\Phi \\ E_{Rx}E_{Rz}(1-\cos\Phi) + E_{Ry}\sin\Phi & E_{Ry}E_{Rz}(1-\cos\Phi) - E_{Rx}\sin\Phi & \cos\Phi + E_{Rz}^2(1-\cos\Phi) \end{bmatrix} \begin{Bmatrix} P_{TMJx} \\ P_{TMJy} \\ P_{TMJz} \end{Bmatrix} \quad (1)$$

where $P'_{TMJx}$, $P'_{TMJy}$, and $P'_{TMJz}$ are components of an opposite TMJ trajectory vector $P'_{TMJ}$, $\Phi$ is any rotation about the TMJ pivot point, $P_{TMJx}$, $P_{TMJy}$, and $P_{TMJz}$ are components of a TMJ position vector $P_{TMJ}$, and a 3×3 rotation matrix, where $E_{rx}$, $E_{ry}$, and $E_{Rz}$ are components of a vector $E_R$ given by the formula:

$$\vec{N}_{P1} = \vec{P}_1 \times \vec{N}_1 \quad (2)$$

$$\vec{N}_{P2} = \vec{P}_2 \times \vec{N}_2 \quad (3)$$

$$\vec{E}_R = \frac{\vec{N}_{P1} \times \vec{N}_{P2}}{|\vec{N}_{P1} \times \vec{N}_{P2}|} \quad (4)$$

where $N_1$ and $N_2$ are normal vectors to the two planes and $P_1$ and $P_2$ are the position vectors from the TMJ pivot point to the normals and $N_{P1}$ and $N_{P2}$ are vector cross products as defined in equations 2 and 3. The TMJ trajectory permits a medical professional to design improved replacement TMJs from the wear surfaces of two lower or upper jaw teeth. The TMJ trajectory permits improved contouring of crowns, caps and bridges. The TMJ trajectory permits improved teeth placement augmentations to improve bite, TMJ functionality and to maximize TMJ motion and to reduce or correct teeth induced stress on the TMJ or on TMJ motion.

The present invention also provides improved TMJ replacement joints designed using the formula of equation (1).

The present invention also provides improved crowns, caps or bridges designed using the formula of equation (1).

The present invention also provides improved mouth guards designed using the formula of equation (1).

The present invention also provides improved teeth alignments using the formula of equation (1).

The present invention also provides improved denture designs using the formula of equation (1).

DESCRIPTION OF THE DRAWINGS

The invention can be better understood with reference to the following detailed description together with the appended illustrative drawings in which like elements are numbered the same:

FIG. 12 depicts a diagram illustrating the jaw rigid body motion;

FIG. 13 depicts that the rotation vector must be in the planes defined by the position and normal vectors to the wear surfaces;

FIGS. 14A&B depict opposite TMJ trajectory constrained to the surface of a sphere centered at the opposite TMJ pivot point with a radius of $|P_{TMJ}|$;

FIGS. 25A&B depict mandibular cavity normal vector correlation for skulls A4, A10, A12, A14, A, Anat and C13 in tabulated form.

DETAILED DESCRIPTION OF THE INVENTION

Figure 1:
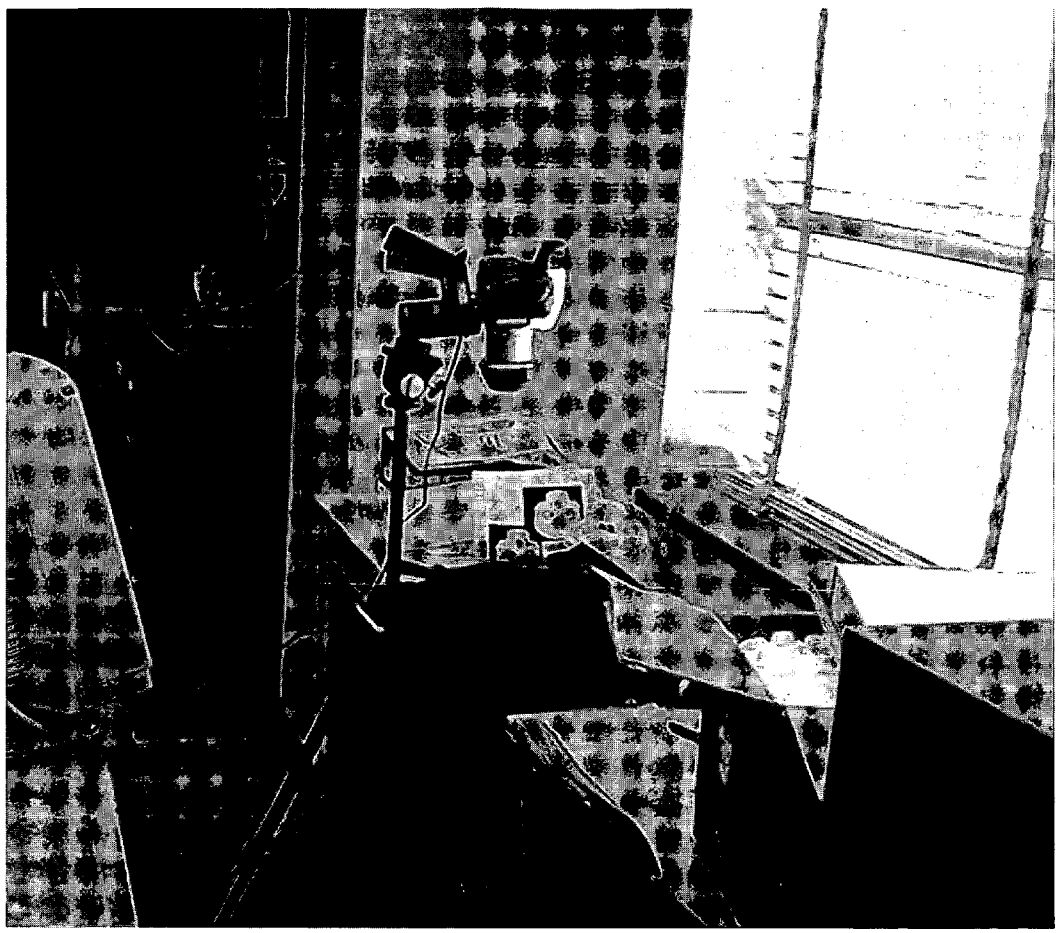
FIG. 1 depicts a photograph of a Sony Mavica MVC-CD1OOO 000 digital camera set a fixed focal length from a skull.

The inventors have found that a mathematical model can be constructed from wear patterns on at least two teeth on opposite side of the jaw to determine and understand temporomandibular joint (TMJ) motion. The determination and understanding of TMJ motion allows the inventors to construct improved dental prostheses such as artificial TMJs, improved caps and/or replacement teeth, or the like and to design improved teeth alignment for orthodontic configurations and improved tooth augmentation to improve or change TMJ dynamics.

The present invention broadly relates to a predictive mathematical formula based on morphometric analysis, analog and/or digital, of a TMJ and teeth of an animal including a human, where the mathematical formula is capable of describing or predicting complex TMJ motion patterns as evidenced by tooth wear and/or jaw wear. Data derived from the formula can then be used to construct remedial appliances or prostheses for the head and neck, and for dental, medical and/or physical therapeutic applications.

The present invention also broadly relates to a method including the step of determining a set of vectors derived from planes of wear of at least two teeth on opposite sides of a jaw and a TMJ pivot point, supplying the vectors to the predictive mathematical formula, deriving a TMJ trajectory model and designing remedial appliances or prostheses for the head and neck, and for dental, medical and/or physical therapeutic applications from the TMJ trajectory model.

Laser Scan and Data Analysis

The inventors investigated the use of a laser scanner technique using a Minolta Laser Scanner made available for initial studies at the research laboratories of Dr. John Kappelman at the University of Texas at Austin, Department of Physical Anthropology. A skull sample was selected from the Department's collection and a trial laser scan was made to test the applicability of the apparatus and to verify that this technique could provide data sufficient to determine the desired relationships and ultimately reduce the relationships to a universal mathematical formula that can be used to predict TMJ motion. From data derived from this formula, improved dental, medical and physical therapeutic treatments of the jaw and teeth can be designed as well as improved prostheses, cap, teeth alignment, teeth resurfacing or other corrective dental procedures.

The sample was scanned using a Minolta Vivid 3-D scanner. The scan was transferred to a digital processing unit, a Dell dual processor work station and was imported into a digital analysis software program called Rapidform available from INUS Technology, Inc. for data analysis and direct measurement determinations.

The trial scan was used to revise the basic thesis and protocols of this invention. We performed a random series of scans of relevant dry specimens in a laboratory facility. The selected specimens came from a private collection of 7 skulls. The seven skulls had been acquired over a period of time and were not collected specifically for this study. Thus, the selection process was random. In addition to these seven skulls, a random selection of skulls from the University of Texas Dental Branch at Houston was also selected.

The selected skulls had to have a fall compliment of teeth and were selected in three categories: (a) youth (deciduous or mixed teeth); (b) adolescent (all permanent teeth with little wear); and (c) adult (permanent teeth in varying stages of wear). Ethnicity was not considered (or known) in the selection process. A group of 24 skulls was selected that fit the basic criteria, grouped as to age and then a non-professional staff member was asked to pick any 6 skulls from the 24 skulls, while the skulls were all closed in their skull cases, i.e., the skulls were not visible.

With skulls in hand, each skull was photographed at a standardized, fixed, focal length and then scanned from the inferior surface using the Minolta Vivid 3-D scanner. The scanning process surveyed the base of the skull, the glenoid fossa, the occipital tubercle, the surfaces of the teeth and the hard palate. No mandibles were scanned.

Multiple scans were made of each skull to obtain the surfaces required to complete the study. These scans were assembled into single composite 3-D images which could be manipulated as needed. The composite 3-D images were compared to the physical specimens for accuracy of detail and measurement.

These images were then used, with the appropriate software, to make linear, angular, and complex spherical studies of multiple surfaces in the 3-D composite images. Of particular interest in the early analyses was to find a mathematical solution for correlated angular function of the wear surfaces of teeth (facets) and the guide (glide) angle of the medial aspect of the glenoid fossa, Zola's Tubercle. See Zola A and Rothschild E. A., *J. Pros Dent.*, "Posterior Condyle Positions in Unimpeded Jaw Movements," 1962, September-October, Vol. II, No. 5, pp 873-881.

The use of non-linear mathematic analysis for solving for angular relationships with 6 degrees of freedom has demonstrated a positive relationship to these areas shaped by dental occlusal function. This work is original; no comparable work is seen in the research literature.

Protocol

Figure 2:
FIG. 2 depicts the image being digitally scanned using a Minolta Vivid 3-D laser scanner.
Figure 3:
FIG. 3 depicts importation of the digitized image into a Dual Processor Dell workstation and assembled into 3-D image processing software.

Skulls used in the study were photographed at a fixed focal length using a Sony Mavica MVC-CD1000 digital camera as shown in FIG. 1 and then digitally scanned using a Minolta Vivid 3-D laser scanner as shown in FIG. 2. The scans were imported into a Dual Processor Dell workstation and assembled into manipulatable 3-D images using INUS Technology, Inc., Rapidform software as shown in FIG. 3.

Figure 4:
FIG. 4 depicts the scanned surfaces selected for analysis from the skull image.
Figure 5:
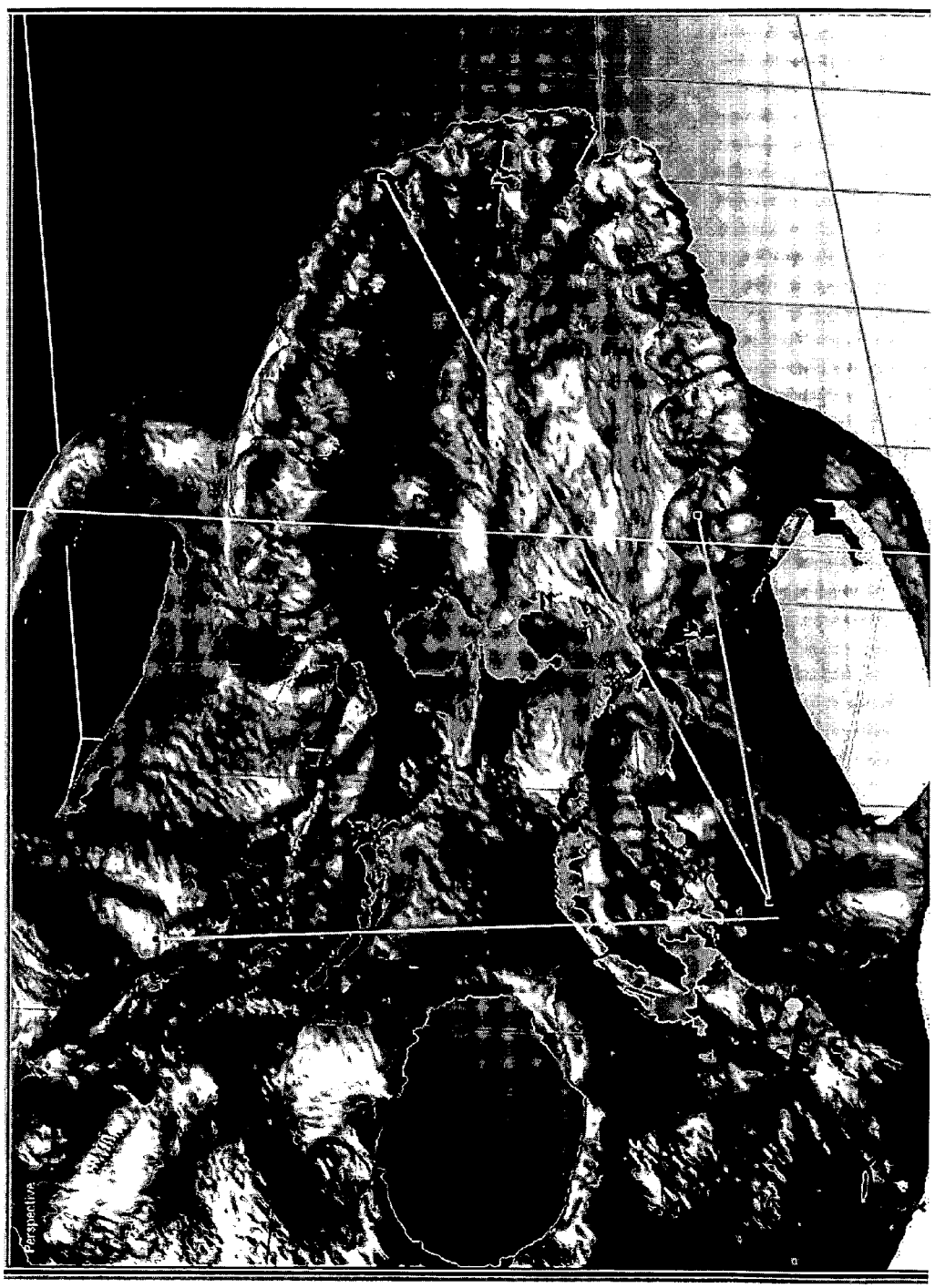
FIG. 5 depicts the digital composite of the skull and the vectors required by the invention to determine and TMJ trajectory equation.
Figure 6:
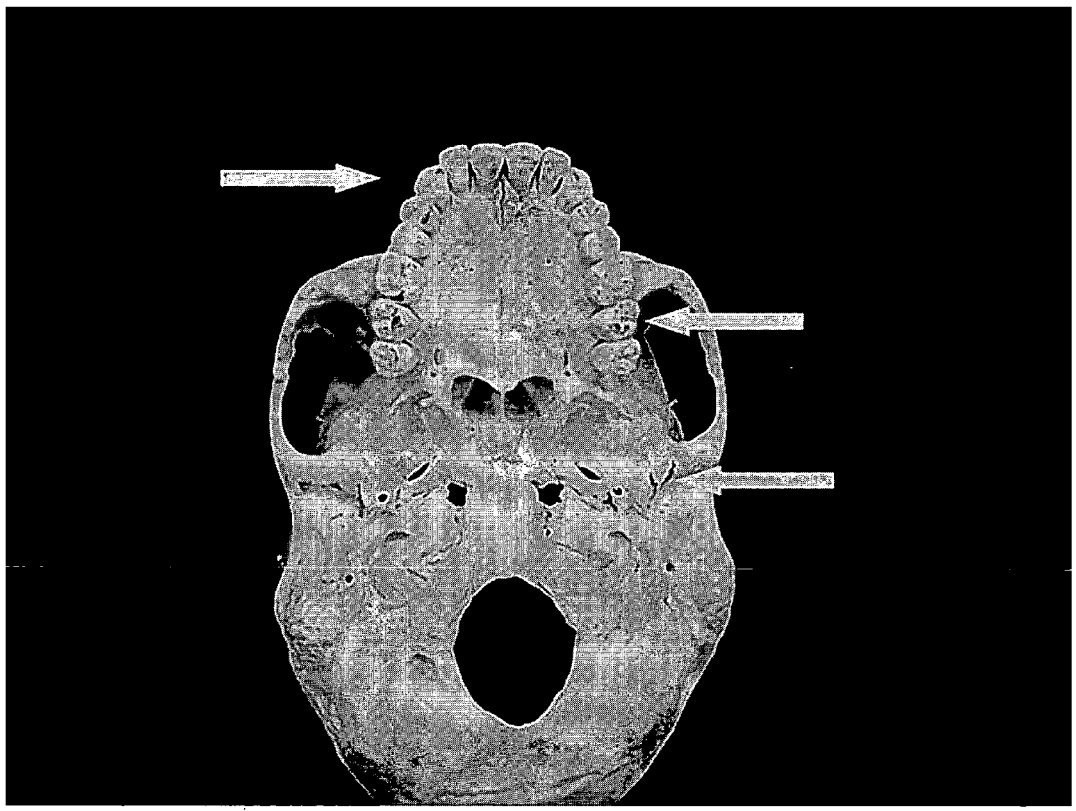
FIG. 6 depicts specific areas of interest of a medial wall of a glenoid fossa on a moving or gliding side, a posterior tooth contact on an ipsilateral side and an anterior tooth on an opposite or contralateral side.

Specific areas of interest on scanned surfaces were selected for analysis as shown in FIG. 4—skull and as shown in FIG. 5—digital composite. The areas identified had been previously marked in dynamic function using an inked red silk ribbon. The specific areas of interest were a medial wall of a glenoid fossa on a moving or gliding side, a posterior tooth contact on an ipsilateral side and an anterior tooth on an opposite or contralateral side as shown in FIG. 6.

Figure 7:
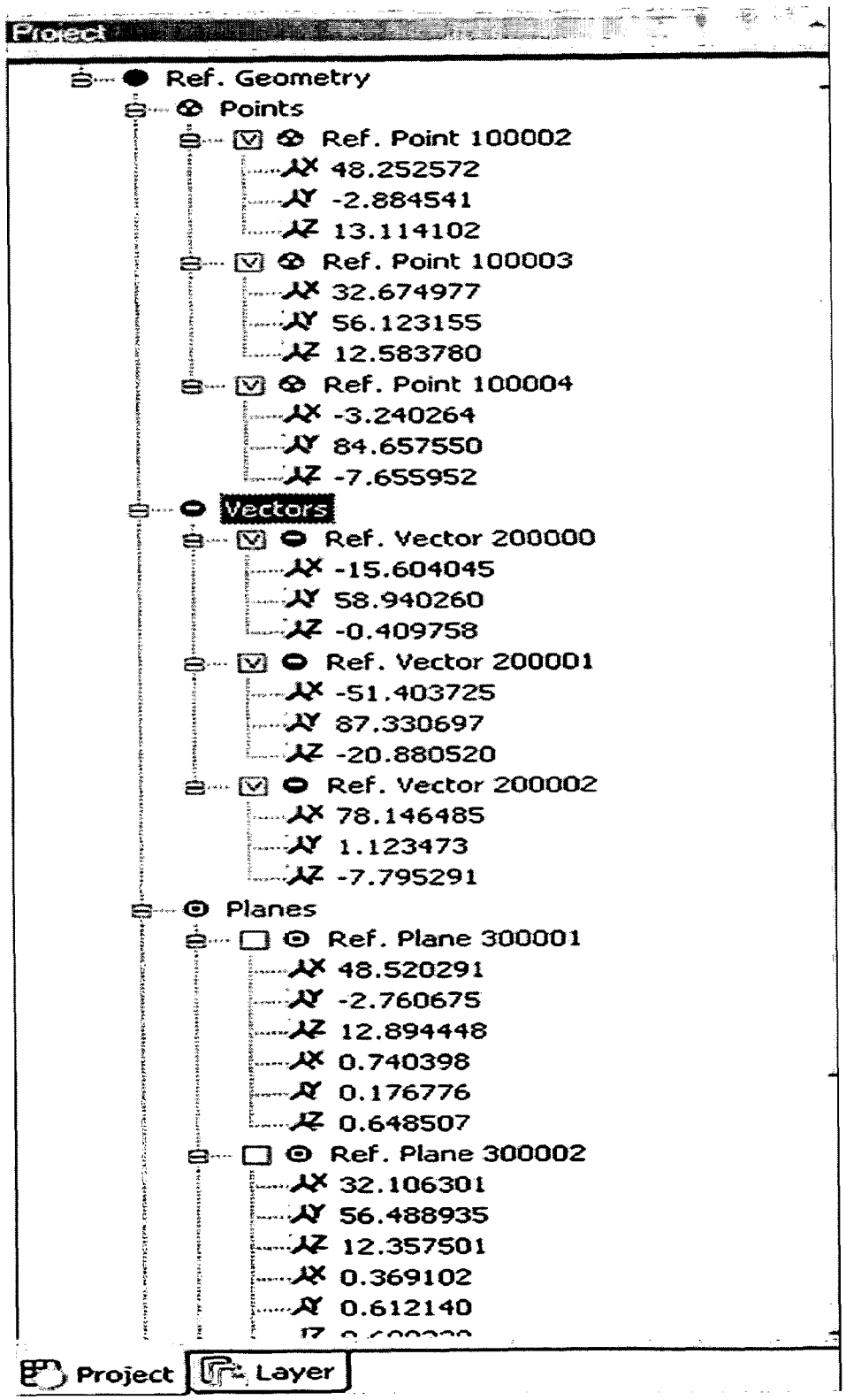
FIG. 7 depicts spherically oriented locations of selected planes of contact.
Figure 8:
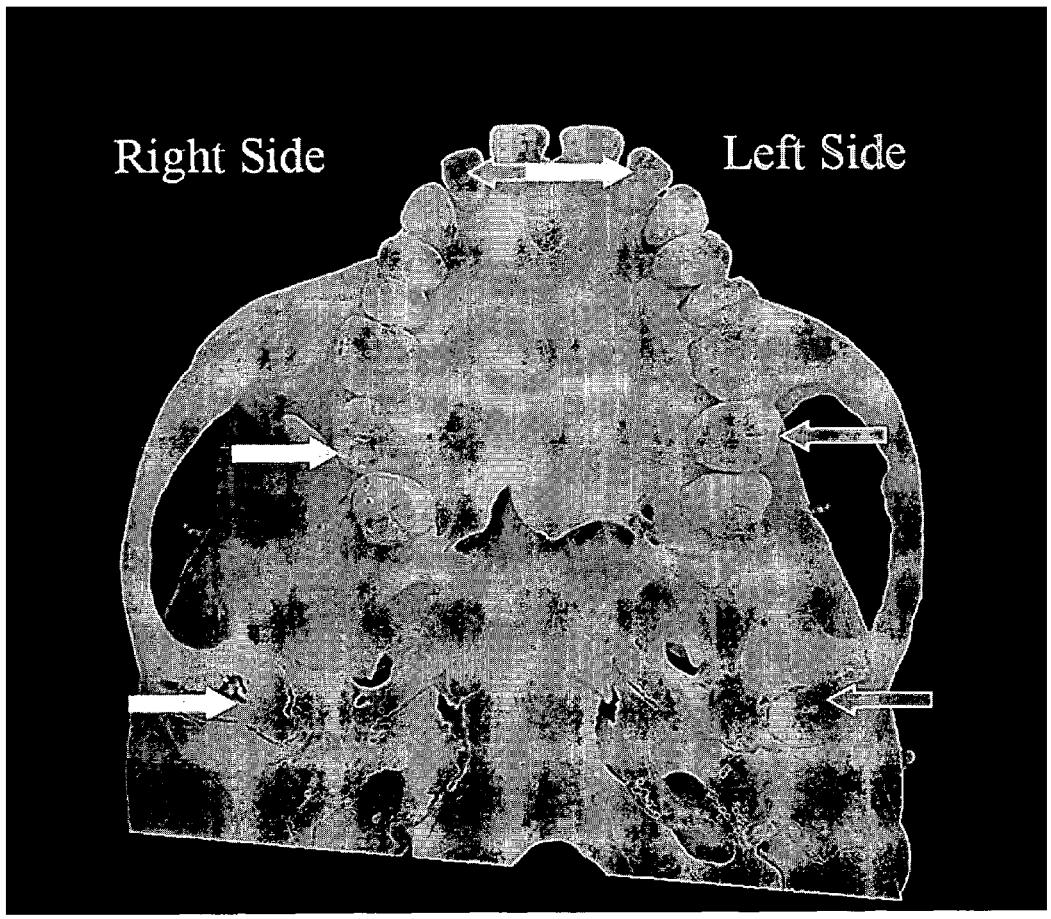
FIG. 8 depicts areas selected for analysis by the image processing software.
Figure 9:
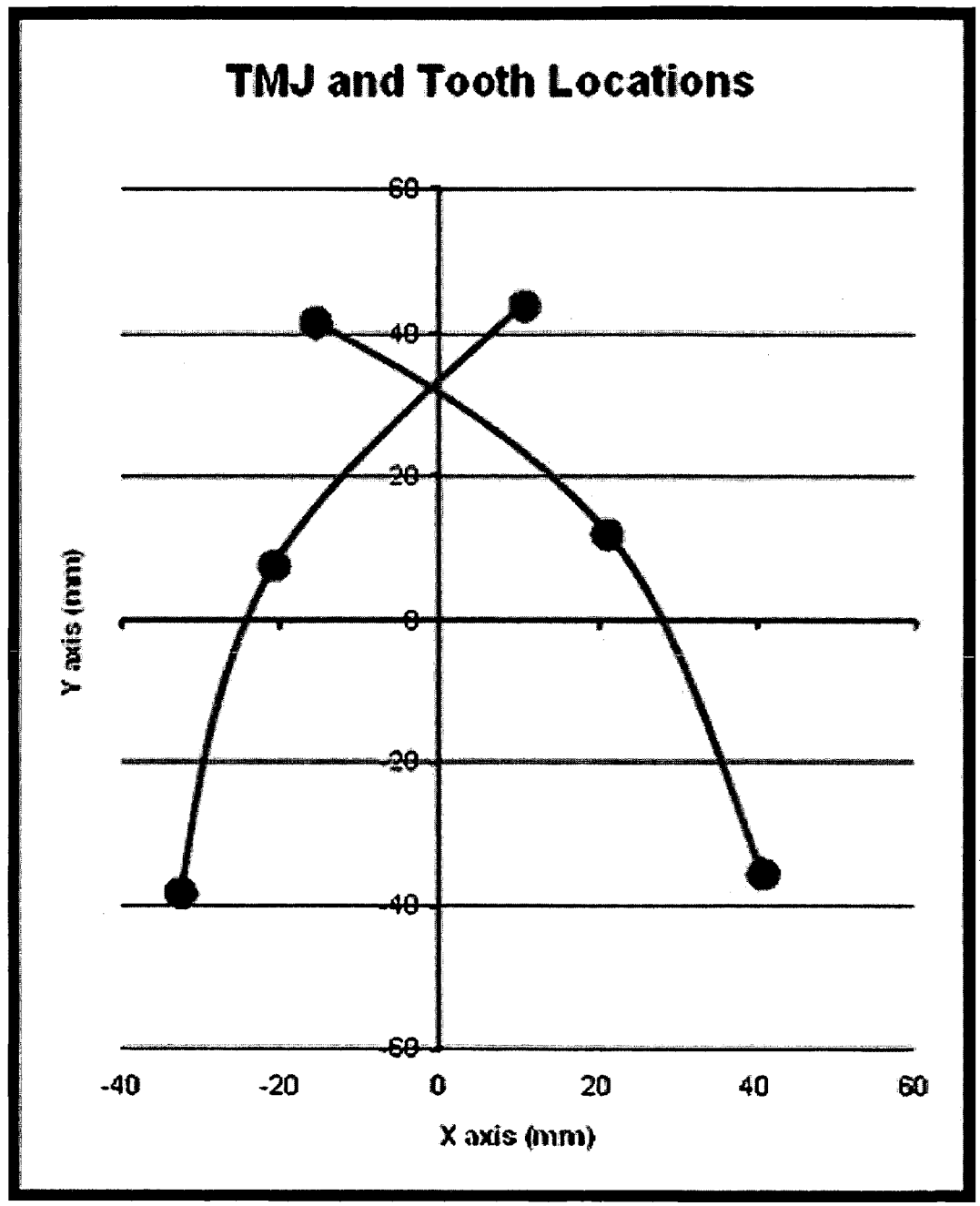
FIG. 9 depicts a plot of a mathematical model showing excellent correlation.

Areas of coordinated functional contacts were mapped by the imaging program which, then, provided detailed mapping coordinates of these specific areas as shown in FIG. 7—data chart. The data were analyzed using linear and non-linear geometric techniques for complex mathematical analyses. The first goal was to make a mathematical model that would transpose the scanned data in a computer model to plot the selected points of function and then to demonstrate the accuracy of these plots as shown in FIGS. 8 and 9—skull and plot photo's. This series of analyses showed the greater majority of the digital data correlated with the scanned data and the physical model of the skull. Where discrepancies were found, we assumed that the selected scan was inconsistent with the anatomical model and reassessment of the scanned images corrected the discrepancy. The study continued with more than 80% of the data being accurate.

In conclusion, this series of studies substantially proved that the digital scans provide sufficient data to locate contact planes of functioning surfaces on teeth (wear facets) and the glenoid fossa (Zola's tubercle). See Zola A and Rothschild E. A., *J Pros Dent.*, "Posterior Condyle Positions in Unimpeded Jaw Movements," 1962, September-October, Vol. II, No. 5, pp 873-881.

Derivation of Formula

Melvin Moss posited the "Functional Matrix" in several papers in the 1970's. In Dental Clinics of North America, (Moss Melvin L, DCNA, *A Functional Cranial Analysis of CentriC Relation,* 1975,0 I,. Vol., L9, No. 3 pp 431-442), Melvin clearly described the functional relationship between muscles and the joints they operate. Melvin described the adaptation of the boney matrix to the dynamics and strength of muscle function.

This concept was then applied to the dynamics of motion and bony architecture of the TMJ. Zola described a functional guiding plane on the medial wall of the glenoid fossa-now called Zola's tubercle. Zola A and Rothschild E. A., J Pros Dent., *Posterior Condyle Positions in Unimpeded Jaw Movements, r962,* September-October, Vol. II, No. 5, PP 873-881.

The inventors have found that the motion of the mandible in the chewing function is controlled by the strength of the major muscles used in food mastication and in the guide planes of contacting teeth and the angle of guidance in the TM joint, more specifically, Zola's tubercle can be used to construct a predictive TMJ joint operational model. The contact of the teeth in forceful use (mastication and/or bruxism or thegosis) moderate and coordinate the power of muscle contraction and these combined forces influence the pressure within the gliding TM joint which effects modification of the boney surfaces, through adaptive change, to be in harmony with the guiding teeth.

The techniques of measurement, data collection and confirmation were described. Using data from physical examination of human dry specimen skulls (digital laser scan images) described above, a mathematical formula to solve the complex relationships of contact and function was determined using non-linear vector mathematical analysis.

To confirm that a single mathematical model could determine the motion of an TMJ, two separate problems had to be solved and the results related.

The derivation of the mathematical equation or mathematical model that permits an understanding and determination of the functioning of the TMJ under normal and forceful use can then be used to construct improved TMJ prostheses, improved crown, cap and bridge designs, improve teeth placement augmentation (orthodontic) and improve mouth guards to correct, prevent or reduce damage to the TMJ. The model can also be used to determine proper reconstruction and/or augmentation surgical procedures.

Figure 10:
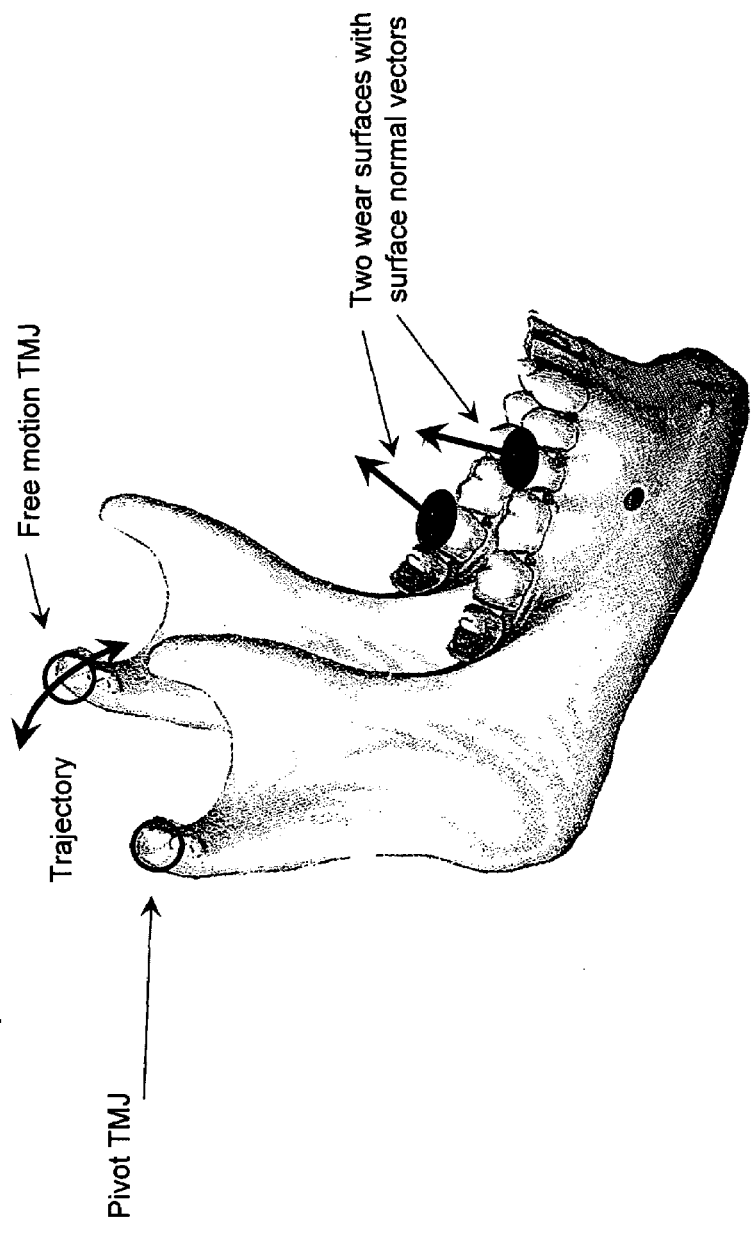
FIG. 10 depicts a diagram of the TMJ pivot and the two wear surface planes of interest.
Figure 11:
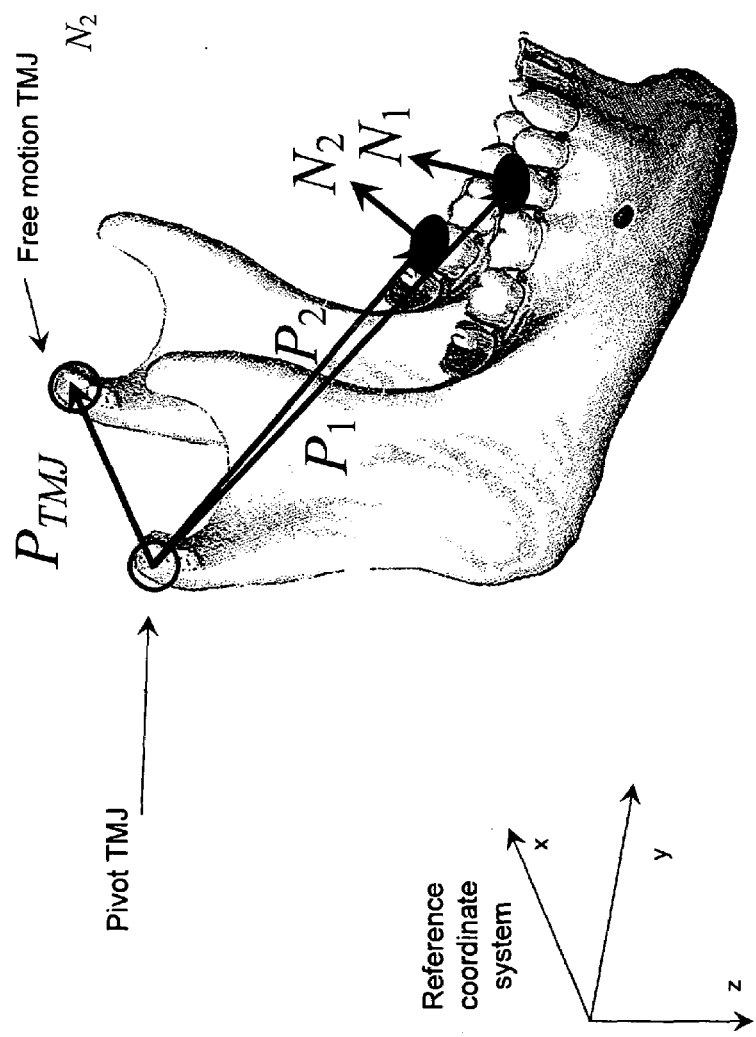
FIG. 11 depicts a diagram of the position, normal and TMJ vectors.

The basic realization leading to the mathematical model was that jaw motion about the TMJ pivot is constrained by wear surfaces on two specific teeth as shown in FIG. 10. The geometry is defined by position vectors ($P_1$ and $P_2$) and normal vectors ($N_1$ and $N_2$) and a TMJ vector ($P_{TMJ}$) as shown in FIG. 11. The jaw rigid body motion is defined by a rotation about a directional vector at the TMJ pivot as shown in FIG. 12. The rotation vector must be in the planes defined by the position vectors and the normal vectors to the wear surfaces as shown in FIG. 13.

The equations that model the motion are given below:

$$\vec{N}_{P1} = \vec{P}_1 \times \vec{N}_1 \quad (2)$$

$$\vec{N}_{P2} = \vec{P}_2 \times \vec{N}_2 \quad (3)$$

$$\vec{E}_R = \frac{\vec{N}_{P1} \times \vec{N}_{P2}}{|\vec{N}_{P1} \times \vec{N}_{P2}|} \quad (4)$$

$$\begin{Bmatrix} P'_{TMJx} \\ P'_{TMJy} \\ P'_{TMJz} \end{Bmatrix} = \begin{bmatrix} \cos\Phi + E_{Rx}^2(1-\cos\Phi) & E_{Rx}E_{Ry}(1-\cos\Phi) + E_{Rz}\sin\Phi & E_{Rx}E_{Rz}(1-\cos\Phi) - E_{Ry}\sin\Phi \\ E_{Rx}E_{Ry}(1-\cos\Phi) - E_{Rz}\sin\Phi & \cos\Phi + E_{Ry}^2(1-\cos\Phi) & E_{Ry}E_{Rz}(1-\cos\Phi) + E_{Rx}\sin\Phi \\ E_{Rx}E_{Rz}(1-\cos\Phi) + E_{Ry}\sin\Phi & E_{Ry}E_{Rz}(1-\cos\Phi) - E_{Rx}\sin\Phi & \cos\Phi + E_{Rz}^2(1-\cos\Phi) \end{bmatrix} \begin{Bmatrix} P_{TMJx} \\ P_{TMJy} \\ P_{TMJz} \end{Bmatrix} \quad (1)$$

where $P'_{TMJx}$, $P'_{TMJy}$, and $P'_{TMJz}$ are components of an opposite TMJ trajectory vector $P'_{TMJ}$, $\Phi$ is any rotation about the TMJ pivot point, $P_{TMJx}$, $P_{TMJy}$, and $P_{TMJz}$ are components of the TMJ position vector $P_{TMJ}$, and a 3×3 rotation matrix set forth in brackets. In the rotation matrix, $E_{rx}$, $E_{ry}$, and $E_{Rz}$ are components of a vector $E_R$, $N_1$ and $N_2$ are the normals to the planes and $P_1$ and $P_2$ are the position vectors from the TMJ pivot to the normals and $N_{P1}$ and $N_{P2}$ are vector cross products as described in. The opposite TMJ trajectory is constrained to the surface of a sphere centered at the opposite TMJ pivot point with a radius of $|P_{TMJ}|$ as shown in FIGS. 14A and 14B. Input data provided via Excel spread sheet: location coordinates for TMJ; location coordinates for constraint teeth, and normal vectors for wear surfaces on constraint teeth. TMJ trajectories plotted on y-z side view along the y reference axis. Trajectories are reported as displacement from the jaw center configuration and left TMJ and right TMJ plotted separately.

A mathematical model was constructed to solve for anyone of three missing guide planes given the other two. In the initial study, the givens were two tooth contacts on opposite sides of the arch and the solution was for the TMJ guide plane. The accuracy of the mathematical model was calculated at 0.99611%, an error factor of 0.088102% (less than 1%), and the solution for the guide angle of Zola's tubercle was consistent with the analog model.

Initial conclusion that can be drawn from this study: (a) There are cross arch tooth contacts which guide the motion of the mandible; (b) The tooth contacts modify muscle function—speed, trajectory and power; (c) TMJ boney surfaces adapt to this muscle function to guide the jaw in harmony with the guidance of the teeth in forceful use of the masticatory system.

Figure 15A:
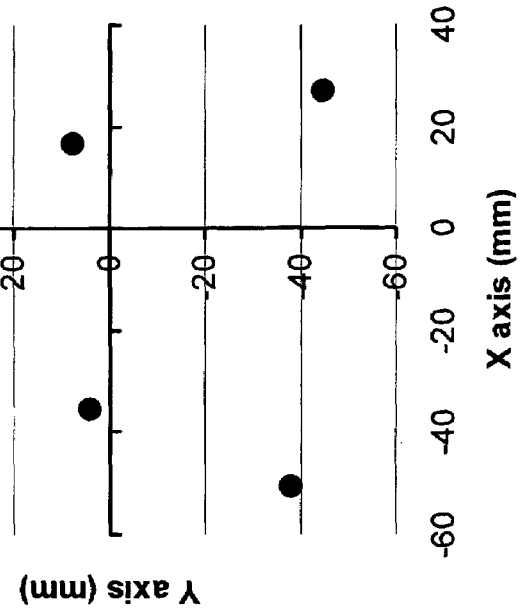
FIGS. 15A&B depict test case study for the A4 skull, TMJ and tooth locations, and TMJ trajectories.
Figure 15B:
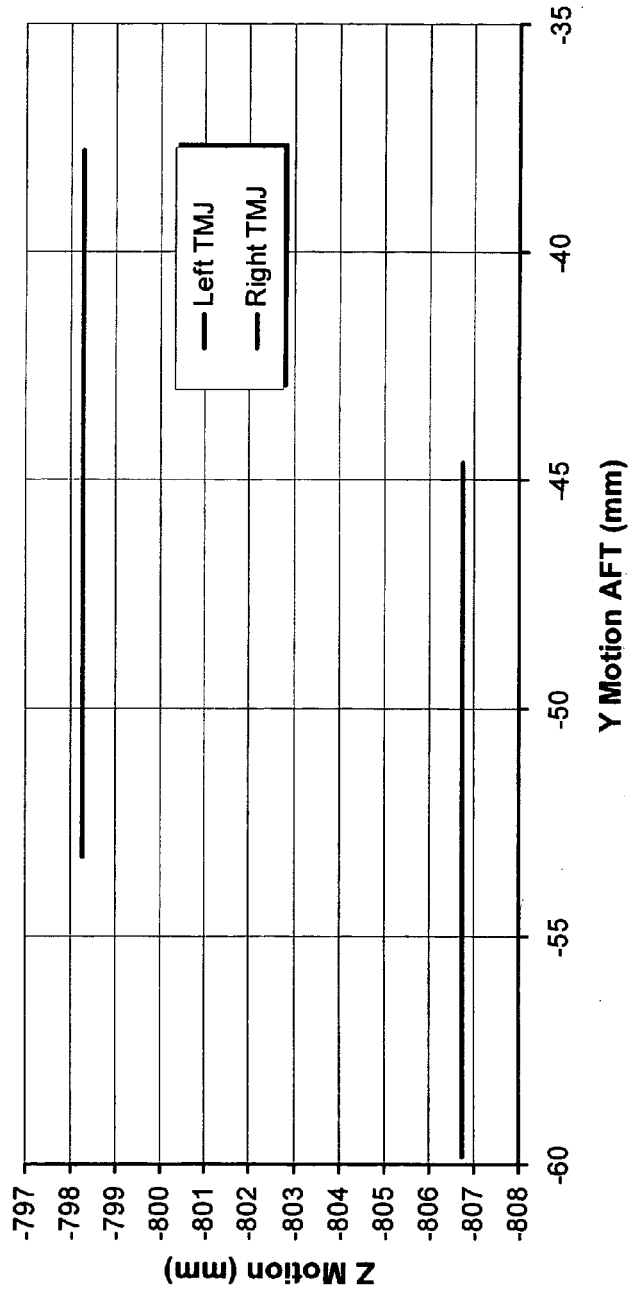

Utilizing the A4 skull data to build simplified trajectory test case: TMJ and tooth location unchanged; normal wear surfaces are horizontal; and TMJ trajectory normal vectors are simple normalization of relative position vectors X and Y components from opposite TMJ and horizontal motion normal vector Z component should be zero. TMJ trajectories should result in a pure horizontal motion. TMJ trajectory normal vectors should coincide with relative position vector X and Y components. Referring now to FIGS. 15A&B, test data for the A4 skull, TMJ and tooth locations, and TMJ trajectories of skull sample A4. The TMJ trajectory test case results are as follows: calculated TMJ trajectories are purely horizontal; calculated trajectory normal vectors coincide exactly with relative position vector constraints—edata is the normal vector input data—normal is the calculated value:

$$edat = \begin{vmatrix} 0.9961111 \\ 0.088102 \\ 0 \end{vmatrix}$$

$$normal = \begin{vmatrix} 0.996111 \\ 0.008102 \\ 0 \end{vmatrix}$$

The mathematical trajectory model yields the expected results for the simplified test case.

Figure 16A:
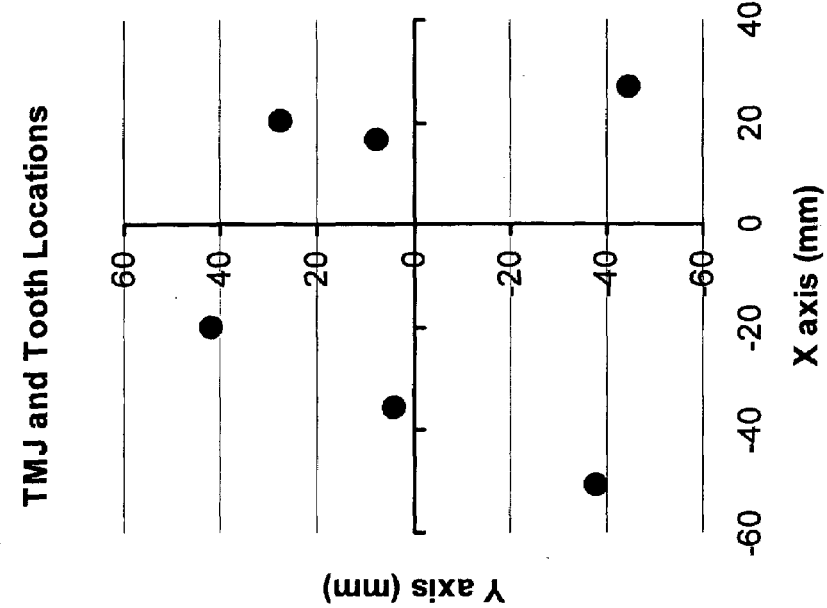
FIGS. 16A&B depict an actual case study for the A4 skull, TMJ and tooth locations, and TMJ trajectories.
Figure 16B:
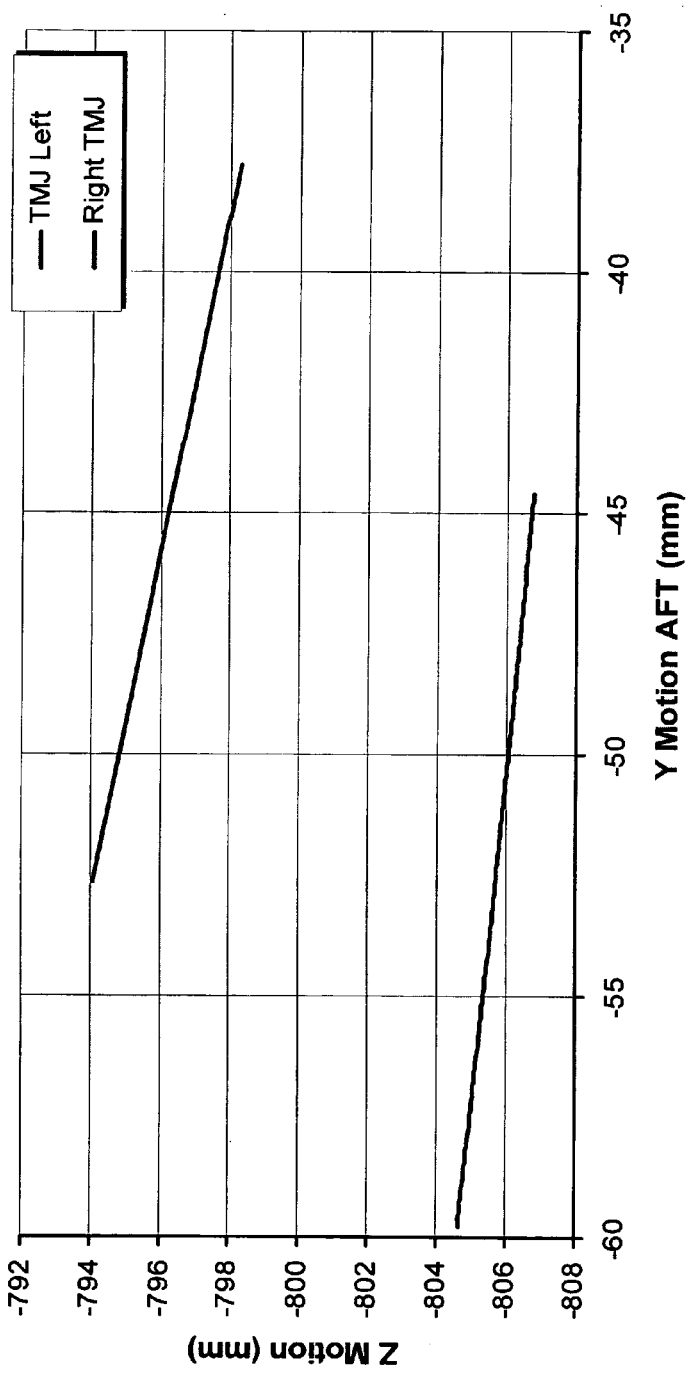

Referring now to FIGS. 16A&B, actual case data for the A4 skull, TMJ and tooth locations, and TMJ trajectories of skull sample A4. The TMJ trajectory test case results are as follows: calculated TMJ trajectories are purely horizontal; calculated trajectory normal vectors coincide exactly with relative position vector constraints.

Figure 17A:
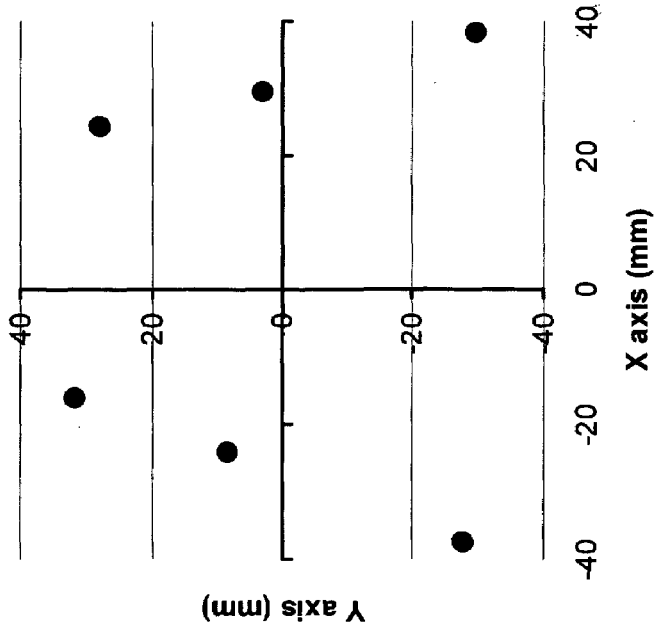
FIGS. 17A&B depict an actual case study for the A10 skull, TMJ and tooth locations, and TMJ trajectories.
Figure 17B:
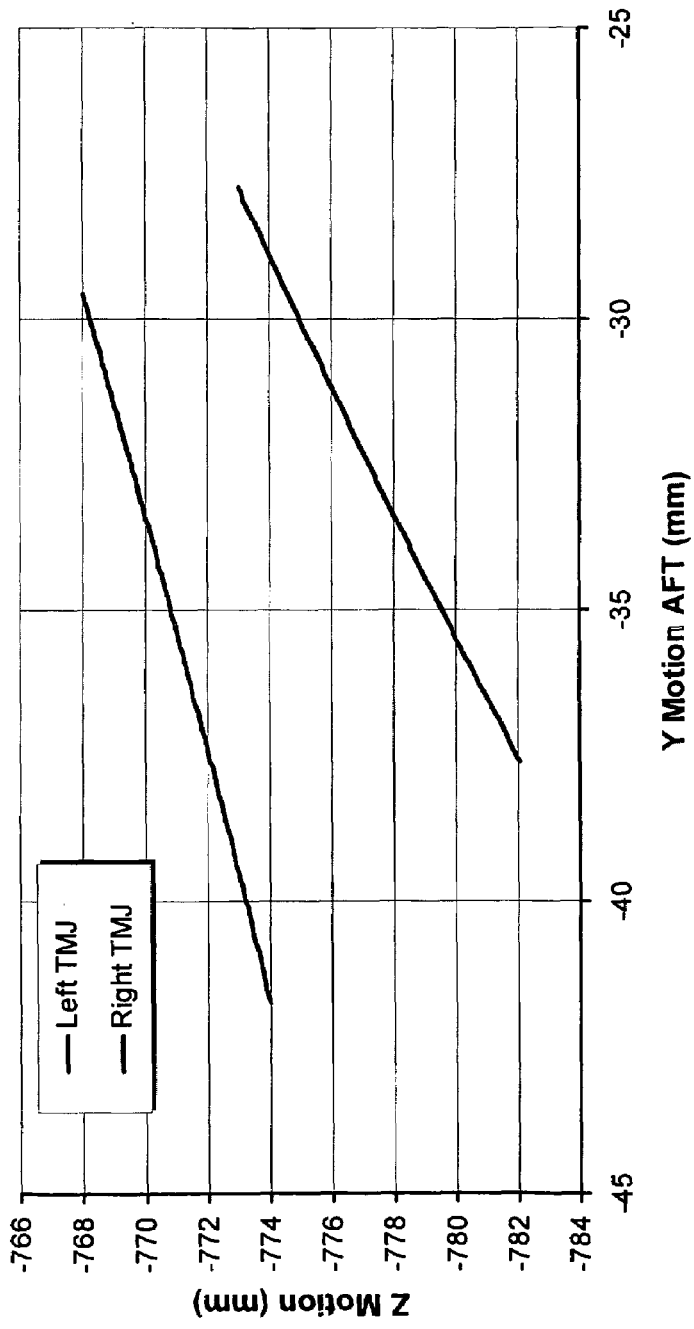

Referring now to FIGS. 17A&B, actual case data for the A4 skull, TMJ and tooth locations, and TMJ trajectories of skull sample A10. The TMJ trajectory test case results are as follows: calculated TMJ trajectories are purely horizontal; calculated trajectory normal vectors coincide exactly with relative position vector constraints.

Figure 18A:
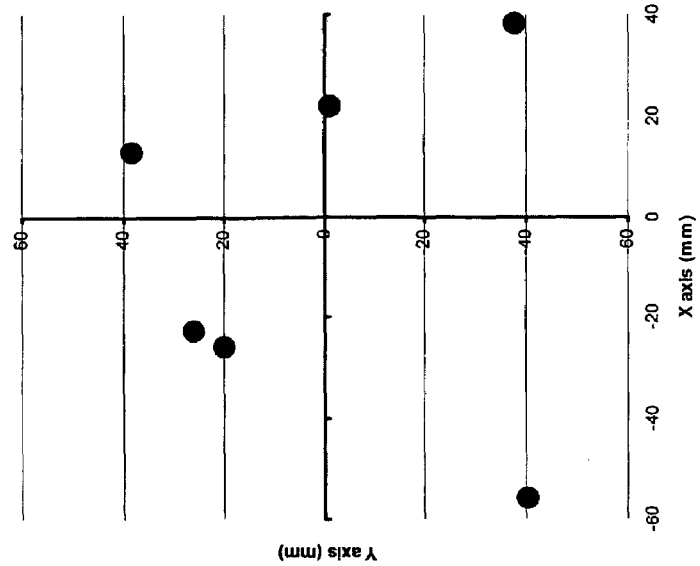
FIGS. 18A&B depict an actual case study for the A12 skull, TMJ and tooth locations, and TMJ trajectories.
Figure 18B:
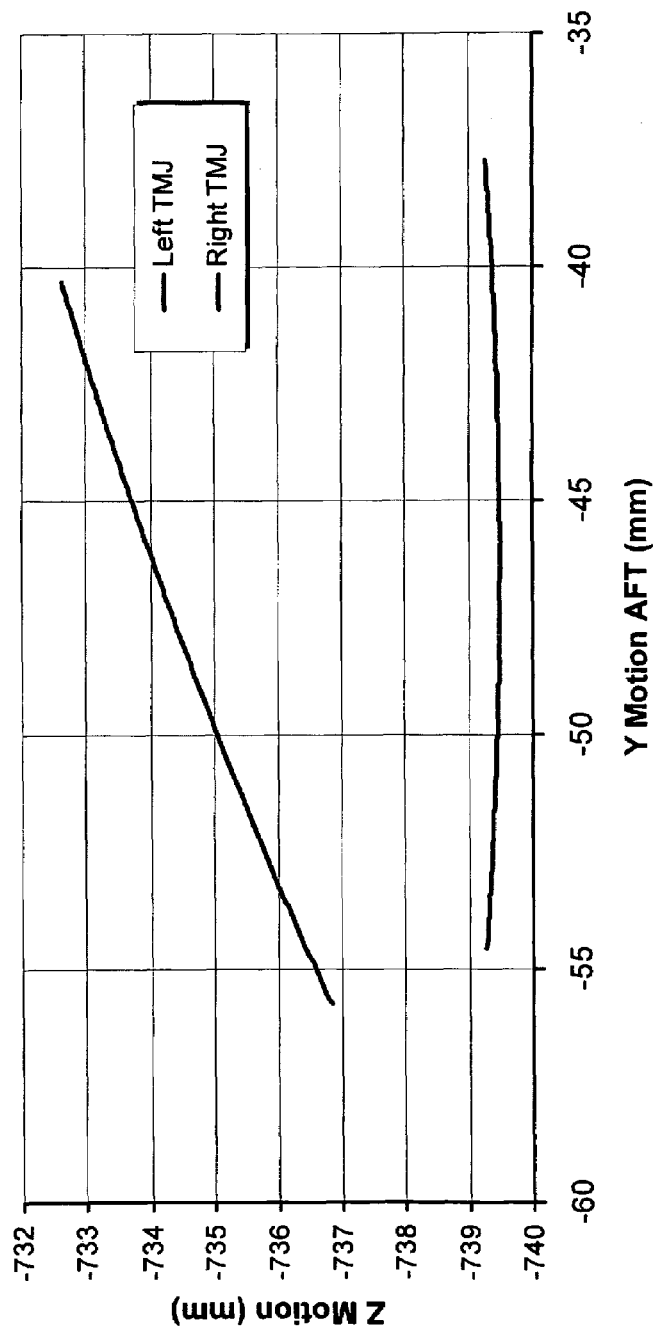

Referring now to FIGS. 18A&B, actual case data for the A4 skull, TMJ and tooth locations, and TMJ trajectories of skull sample A12. The TMJ trajectory test case results are as follows: calculated TMJ trajectories are purely horizontal; calculated trajectory normal vectors coincide exactly with relative position vector constraints.

Figure 19A:
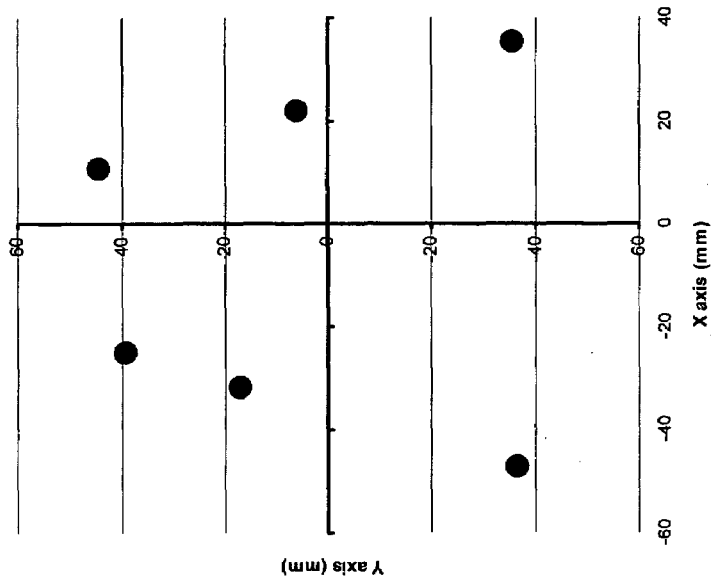
FIGS. 19A&B depict an actual case study for the A14 skull, TMJ and tooth locations, and TMJ trajectories.
Figure 19B:
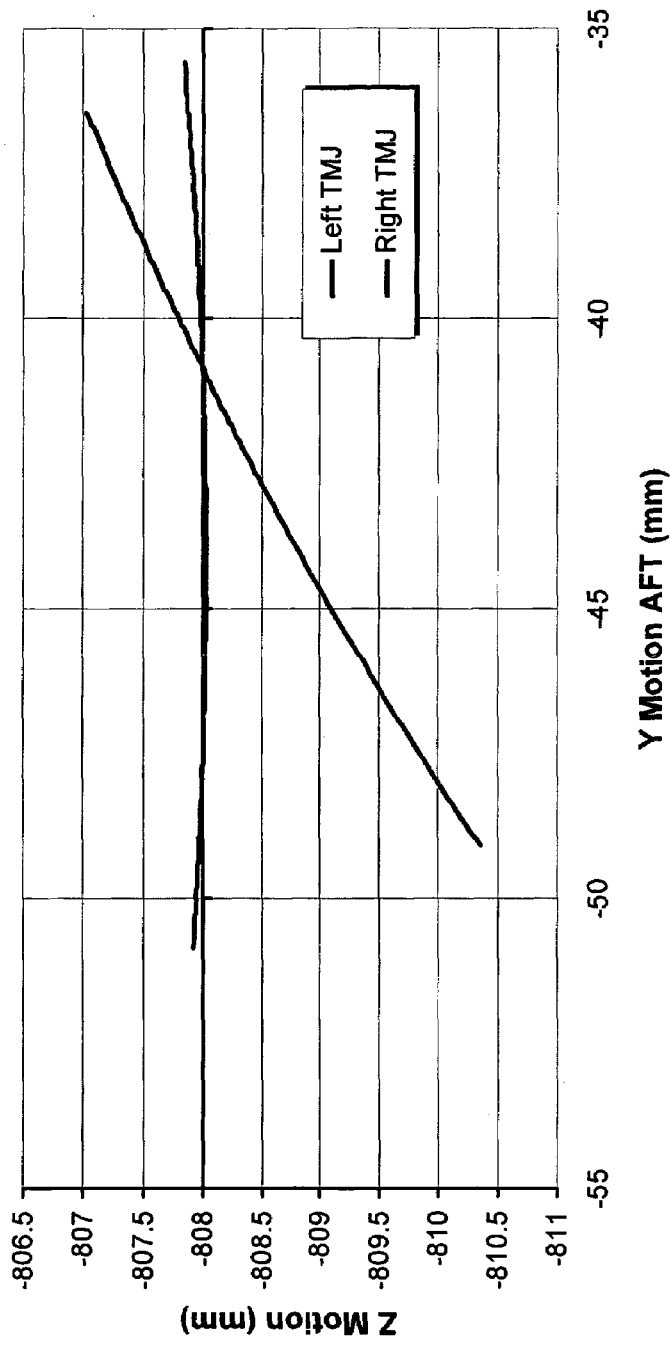

Referring now to FIGS. 19A&B, actual case data for the A4 skull, TMJ and tooth locations, and TMJ trajectories of skull sample A14. The TMJ trajectory test case results are as follows: calculated TMJ trajectories are purely horizontal; calculated trajectory normal vectors coincide exactly with relative position vector constraints.

Figure 20A:
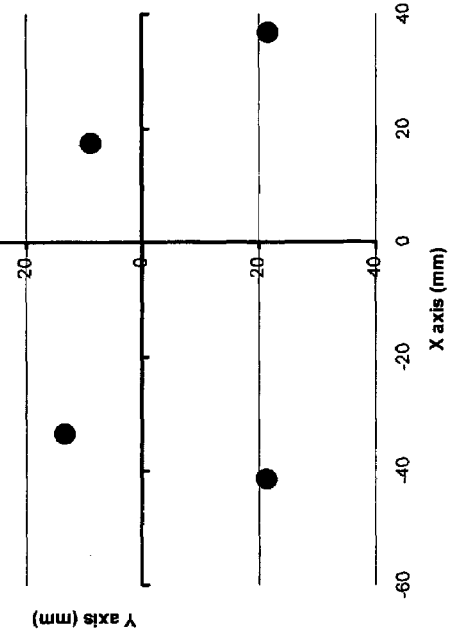
FIGS. 20A&B depict an actual case study for the A skull, TMJ and tooth locations, and TMJ trajectories.
Figure 20B:
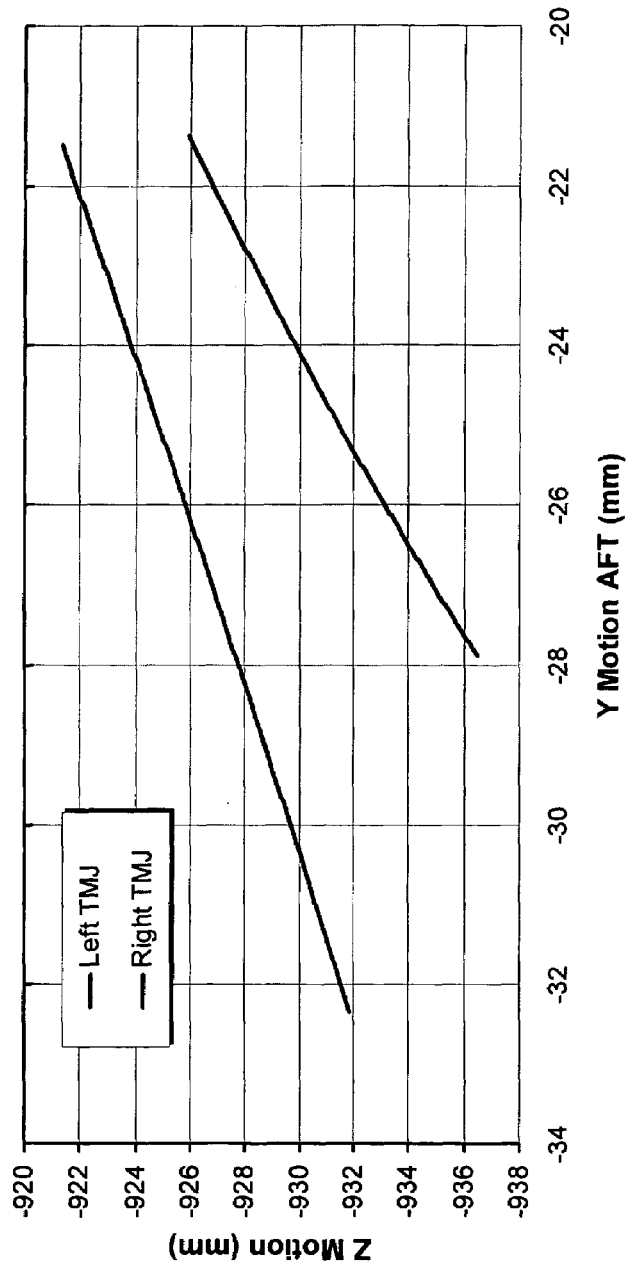

Referring now to FIGS. 20A&B, actual case data for the A4 skull, TMJ and tooth locations, and TMJ trajectories of skull sample A. The TMJ trajectory test case results are as follows: calculated TMJ trajectories are purely horizontal; calculated trajectory normal vectors coincide exactly with relative position vector constraints.

Figure 21A:
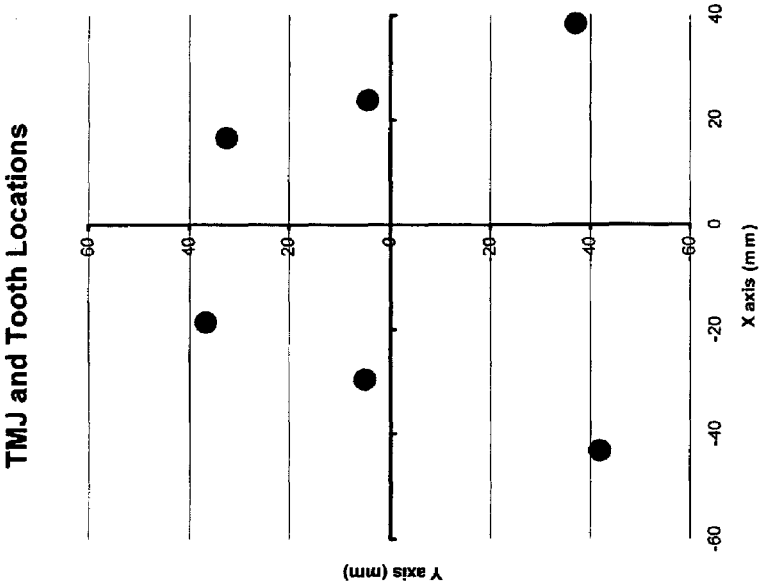
FIGS. 21A&B depict an actual case study for the Anat skull, TMJ and tooth locations, and TMJ trajectories.
Figure 21B:
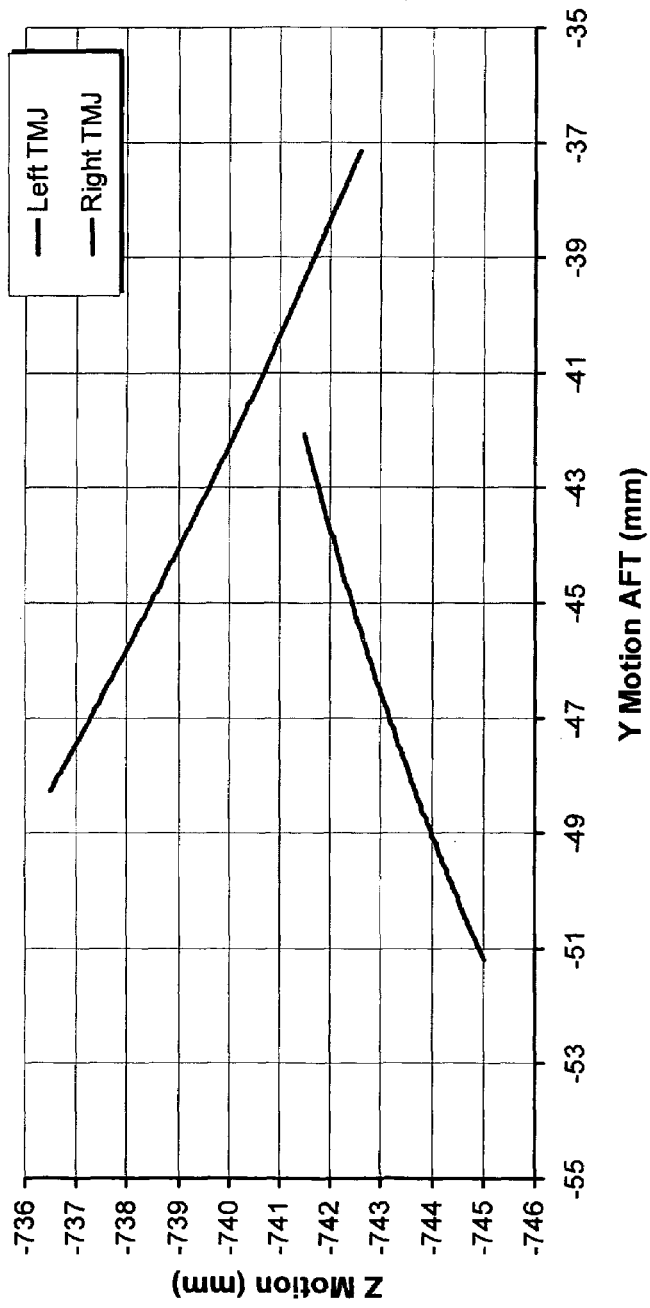

Referring now to FIGS. 21A&B, actual case data for the A4 skull, TMJ and tooth locations, and TMJ trajectories of skull sample Anat. The TMJ trajectory test case results are as follows: calculated TMJ trajectories are purely horizontal; calculated trajectory normal vectors coincide exactly with relative position vector constraints.

Figure 22A:
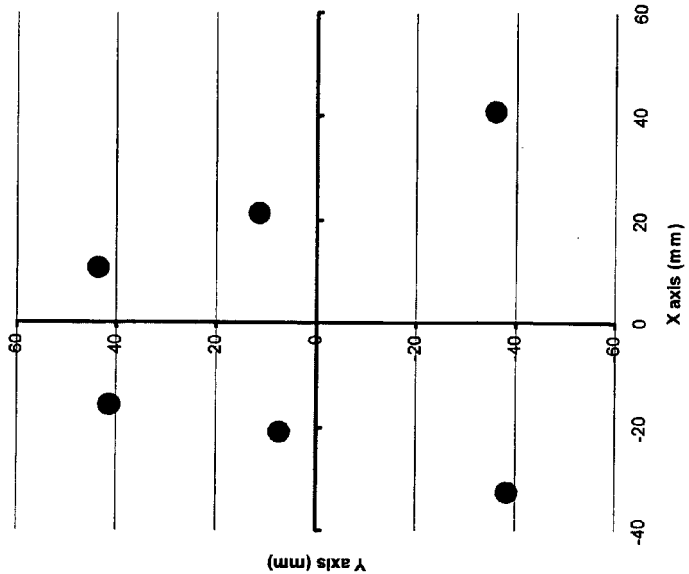
FIGS. 22A&B depict an actual case study for the C13 skull, TMJ and tooth locations, and TMJ trajectories.
Figure 22B:
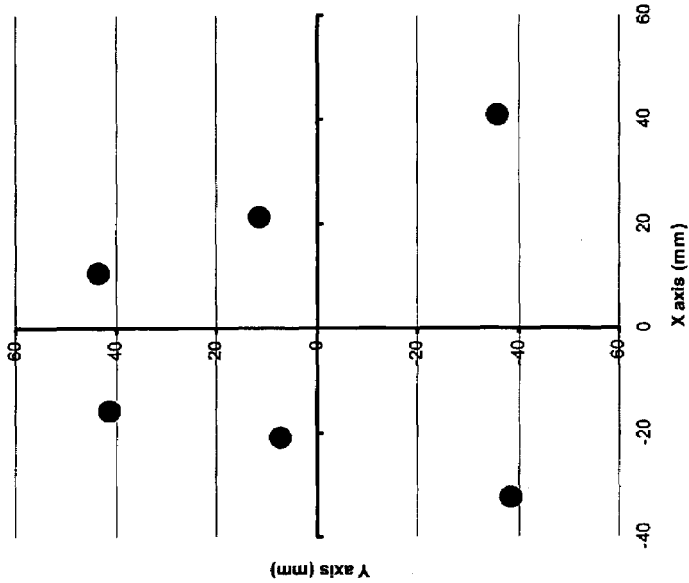

Referring now to FIGS. 22A&B, actual case data for the A4 skull, TMJ and tooth locations, and TMJ trajectories of skull sample C13. The TMJ trajectory test case results are as follows: calculated TMJ trajectories are purely horizontal; calculated trajectory normal vectors coincide exactly with relative position vector constraints.

TMJ Physiological Supposition

The skull structure conforms to TMJ motion, adjusting over time. Because of this conformity, the inventors expected a correlation to exist between the predicted TMJ trajectories within the mandibular cavity. The data showed that localized skull surfaces conform to the predicted TMJ trajectory and that normal vector to surfaces were theorized to be correlated to normal vector calculated from the TMJ trajectory.

Figure 23:
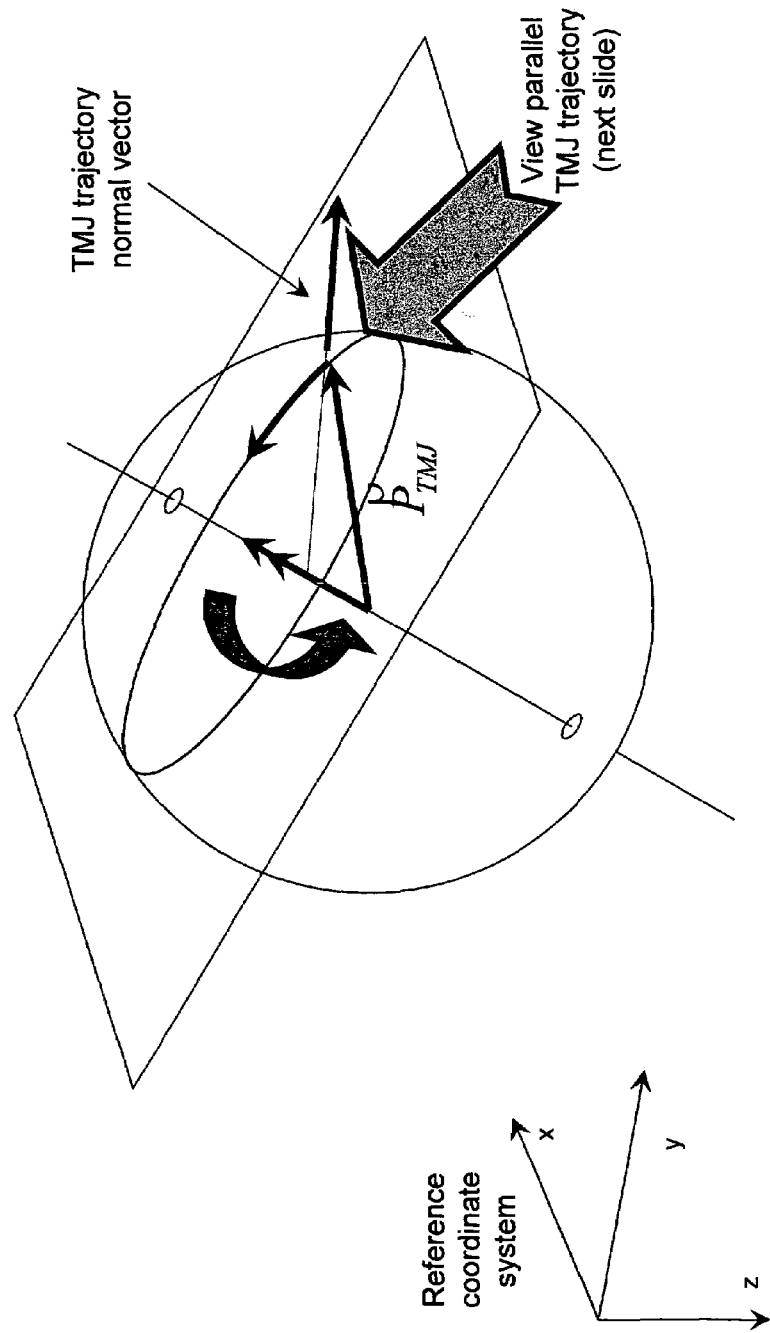
FIG. 23 depicts that the TMJ trajectory normal vector is constrained to the plane of the circular trajectory path.

The TMJ trajectory normal vector is constrained to the plane of the circular trajectory path as shown in FIG. 23.

View Parallel TMJ Trajectory

Figure 24:
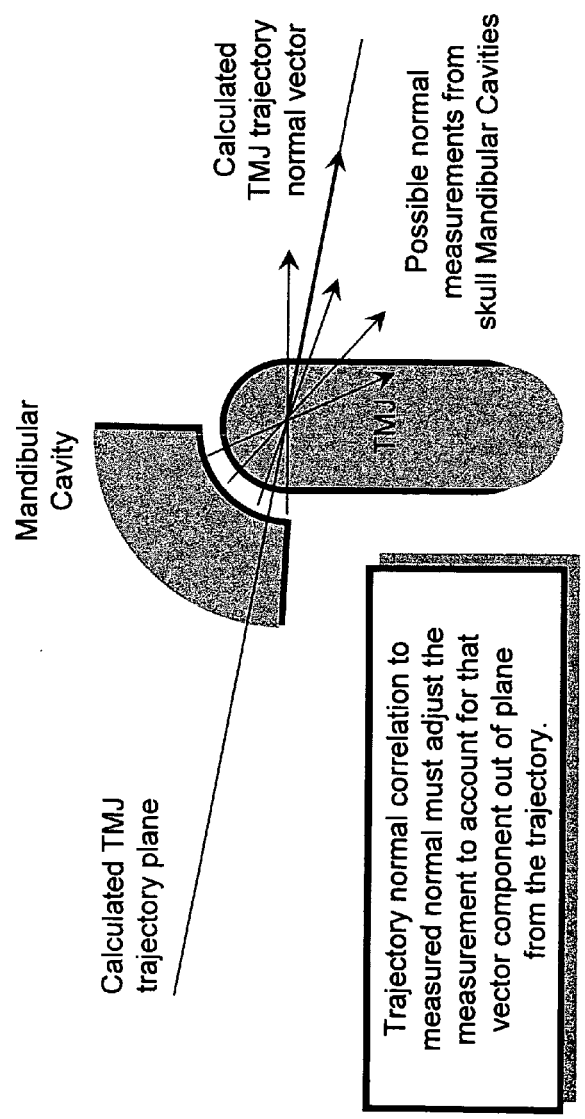
FIG. 24 depicts that multiple possibilities of surface orientations exist between the TMJ and the mandibular cavity.

Multiple possibilities of surface orientations exist between the TMJ and the mandibular cavity as shown in FIG. 24. Trajectory normal correlation to measured normal must adjust the measurement to account for that vector component out of plane from the trajectory as shown in Figure.

Trajectory Normal Vector

The trajectory normal vector is defined via vector mathematics. Calculate the instantaneous trajectory tangent vector and trajectory normal vector is normal to both tangent and the rotation orientation vectors:

$$T_{TMJ} = \frac{\frac{dP_{TMJ}}{d\Phi}}{\left|\frac{dP_{TMJ}}{d\Phi}\right|}$$

$$N_{TMJ} = \frac{T_{TMJ} \times E_R}{|T_{TMJ} \times E_R|}$$

Measured Mandibular Cavity Normal Vector

The measured normal vector is adjusted to remove vector components normal to the calculated trajectory plane. Calculate the normal vector components normal to the calculated TMJ trajectory plane. Subtract from the measured normal and renormalized to unit length:

$$N_{projected} = (E_R \cdot N_{measured}) * E_R$$

-continued $$N_{adjusted} = N_{measured} - N_{projected}$$

$$N_{adjusted} = \frac{N_{adjusted}}{|N_{adjusted}|}$$

Mandidular Cavity Normal Vector Correlation

Referring now to FIGS. 25A&B, mandibular cavity normal vector correlation for skulls A4, A10, A12, A14, A, Anat and C13 are shown in tabulated form. The data indicates that trajectories are highly variable from individual to individual and from jaw to jaw on any particular individual. The data does not support a correlation with mandibular cavity wear surface measured normal vectors. However, the determined variation is proposed to be within selected data collection sites which are to be re-evaluated. The mathematical model is proposed to be accurate and valid.

All references cited herein are incorporated by reference. While this invention has been described fully and completely, it should be understood that, within the scope of the appended claims, the invention may be practiced otherwise than as specifically described. Although the invention has been disclosed with reference to its preferred embodiments, from reading this description those of skill in the art may appreciate changes and modification that may be made which do not depart from the scope and spirit of the invention as described above and claimed hereafter.

We claim:

1. A method for analyzing jaw motion comprising the steps of:

generating images of an upper jaw, a lower jaw, upper teeth, lower teeth and a temporomandibular joint (TMJ) of an animal including a human using an imaging system, creating a 3-D image of the upper jaw, the lower jaw, the upper teeth, the lower teeth and the temporomandibular joint (TMJ) of the animal in a processing unit, determining planes associated with wear surfaces of at least two teeth of an upper jaw or a lower jaw, the selected jaw, from the 3-D image, where at least one of the teeth is located on an ipsilateral posterior side of the selected jaw and at least another one of the teeth is located on a contralateral anterior side of the selected jaw, using routines implemented in the processing unit, calculating normals vector $N_1$ of a wear surface of a tooth on the ipsilateral posterior side of the selected jaw and normal vector $N_2$ of a wear surface of a tooth on the contralateral anterior side of the selected jaw, where each normal vectors are directed towards the non-selected jaw, using routines implemented in the processing unit, determining a position vector $P_1$ between a first temporomandibular joint (TMJ) pivot point and a center point of the wear surface of the tooth on the ipsilateral posterior side of the selected jaw, a position vector $P_2$ between the first temporomandibular joint (TMJ) pivot point and a center point of the wear surface of the tooth on the contralateral anterior side of the selected jaw, and a TMJ position vector $P_{TMJ}$ between the first TMJ pivot point and a second TMJ pivot point; using routines implemented in the processing unit, calculating a vector cross product $N_{P1}$, using routines implemented in the processing unit, $$\vec{N}_{P1} = \vec{P}_1 \times \vec{N}_1$$

calculating a vector cross product $N_2$ using routines implemented in the processing unit, $$\vec{N}_{P2} = \vec{P}_2 \times \vec{N}_2$$

calculating a vector $E_R$, using routines implemented in the processing unit, $$\vec{E}_R = \frac{\vec{N}_{P1} \times \vec{N}_{P2}}{|\vec{N}_{P1} \times \vec{N}_{P2}|}$$

supplying vector components $E_{rx}$, $E_{ry}$, and $E_{Rz}$ of the vector $E_R$ and components $P_{TMJx}$, $P_{TMJy}$, and $P_{TMJz}$ of the vector $P_{TMJ}$ to a temporomandibular joint trajectory equation comprising:

$$\begin{Bmatrix} P'_{TMJx}, \\ P'_{TMJy}, \\ P'_{TMJz}, \end{Bmatrix} =$$

$$\begin{bmatrix} \cos\Phi + E_{Rx}^2(1-\cos\Phi) & E_{Rx}E_{Ry}(1-\cos\Phi) + E_{Rz}\sin\Phi & E_{Rx}E_{Rz}(1-\cos\Phi) - E_{Ry}\sin\Phi \\ E_{Rx}E_{Ry}(1-\cos\Phi) - E_{Rz}\sin\Phi & \cos\Phi + E_{Ry}^2(1-\cos\Phi) & E_{Ry}E_{Rz}(1-\cos\Phi) + E_{Rx}\sin\Phi \\ E_{Rx}E_{Rz}(1-\cos\Phi) + E_{Ry}\sin\Phi & E_{Ry}E_{Rz}(1-\cos\Phi) - E_{Rx}\sin\Phi & \cos\Phi + E_{Rz}^2(1-\cos\Phi) \end{bmatrix}$$

$$\begin{Bmatrix} P_{TMJx} \\ P_{TMJy} \\ P_{TMJz} \end{Bmatrix}$$

where $P'_{TMJx}$, $P'_{TMJy}$, and $P'_{TMJz}$ are components of an opposite TMJ trajectory vector $P'_{TMJ}$, $\Phi$ is any rotation about the first TMJ pivot point, $P_{TMJx}$, $P_{TMJy}$, and $P_{TMJz}$ are components of the TMJ position vector $P_{TMJ}$, and a 3×3 rotation matrix, implemented in the processing unit, and predicting motion of the TMJ from the TMJ trajectory equation using routines implemented in the processing unit.

2. The method of claim 1, further comprising the step of:
constructing improved a dental prostheses based on the predicted TMJ motion to correct, prevent or reduce damage to the TMJ using routines implemented in the processing unit.

3. The method of claim 1, further comprising the step of:
contouring improved crowns, caps or bridges based on the predicted TMJ motion to correct, prevent or reduce damage to the TMJ using routines implemented in the processing unit.

4. The method of claim 1, further comprising the step of:
constructing improved mouth guards based on the predicted TMJ motion to correct, prevent or reduce damage to the TMJ using routines implemented in the processing unit.

5. The method of claim 1, further comprising the step of:
contouring teeth based on the predicted TMJ motion to correct, prevent or reduce damage to the TMJ using routines implemented in the processing unit.

6. A method implemented on a computer for predicting motion of a temporomandibular joint comprising the steps of generating a 3-D image of an upper jaw, a lower jaw, upper and lower teeth and the temporomandibular joint (TMJ) using an imaging system and a processing unit;

locating a right TMJ pivot and left TMJ pivot using routines implemented in the processing unit;

selecting one of the two TMJ pivots, the selected pivot, determining wear planar surfaces for at least two teeth on the upper jaw or lower jaw, the selected jaw, one on an ipsilateral posterior side of the selected jaw and one a contralateral anterior side of the selected jaw using routines implemented in the processing unit;

determining normal vectors to the surfaces pointing toward the non-selected jaw and position vectors between the selected pivot and an opposite side TMJ pivot and between the selected pivot the two normals using routines implemented in the processing unit;

determining a TMJ trajectory according to equation (1) using routines implemented in the processing unit:

$$\begin{Bmatrix} P'_{TMJx}, \\ P'_{TMJy}, \\ P'_{TMJz}, \end{Bmatrix} = \quad (1)$$

$$\begin{bmatrix} \cos\Phi + E_{Rx}^2(1-\cos\Phi) & E_{Rx}E_{Ry}(1-\cos\Phi) + E_{Rz}\sin\Phi & E_{Rx}E_{Rz}(1-\cos\Phi) - E_{Ry}\sin\Phi \\ E_{Rx}E_{Ry}(1-\cos\Phi) - E_{Rz}\sin\Phi & \cos\Phi + E_{Ry}^2(1-\cos\Phi) & E_{Ry}E_{Rz}(1-\cos\Phi) + E_{Rx}\sin\Phi \\ E_{Rx}E_{Rz}(1-\cos\Phi) + E_{Ry}\sin\Phi & E_{Ry}E_{Rz}(1-\cos\Phi) - E_{Rx}\sin\Phi & \cos\Phi + E_{Rz}^2(1-\cos\Phi) \end{bmatrix}$$

$$\begin{Bmatrix} P_{TMJx} \\ P_{TMJy} \\ P_{TMJz} \end{Bmatrix}$$

where $P'_{TMJx}$, $P'_{TMJy}$, and $P'_{TMJz}$ are components of an opposite TMJ trajectory vector $P'_{TMJ}$, $\Phi$ is any rotation about the TMJ pivot, $P_{TMJx}$, $P_{TMJy}$, and $P_{TMJz}$ are components of a TMJ position vector $P_{TMJ}$, a 3×3 rotation matrix set forth in brackets, where $N_1$ and $N_2$ are the normal vectors to the two surfaces and $P_1$ and $P_2$ are the position vectors from the TMJ pivot to the normals and where $N_{P1}$, and $N_{P2}$ are vector cross products and $E_{rx}$, $E_{ry}$ and $E_{Rz}$, are components of a vector $E_R$ given by the formulas:

$$\vec{N}_{P1} = \vec{P}_1 \times \vec{N}_1 \quad (2)$$

$$\vec{N}_{P2} = \vec{P}_2 \times \vec{N}_2 \quad (3)$$

$$\vec{E}_R = \frac{\vec{N}_{P1} \times \vec{N}_{P2}}{|\vec{N}_{P1} \times \vec{N}_{P2}|} \quad (4)$$

predicting motion of the TMJ from the TMJ trajectory equation using routines implemented in the processing unit.

7. The method of claim 6, further comprising the step of:
constructing an improved TMJ replacement joint based on the predicted TMJ motion to correct, prevent or reduce damage to the TMJ using routines implemented in the processing unit.

8. The method of claim 6, further comprising the step of:
contouring improved crowns, caps or bridges based on the predicted TMJ motion to correct, prevent or reduce damage to the TMJ using routines implemented in the processing unit.

9. The method of claim 6, further comprising the step of:
preparing improved mouth guards based on the predicted TMJ motion to correct, prevent or reduce damage to the TMJ using routines implemented in the processing unit.

10. The method of claim 6, further comprising the step of:
aligning teeth using braces based on the predicted TMJ motion to correct, prevent or reduce damage to the TMJ using routines implemented in the processing unit.

11. The method of claim 6, further comprising the step of:
preparing dentures based on the predicted TMJ motion to correct, prevent or reduce damage to the TMJ using routines implemented in the processing unit.

12. A system for determining temporomandibular joint (TMJ) motion of an animal including a human comprising:

an imaging subsystem adapted to generate a 3-D image of an upper jaw, a lower jaw, upper teeth, lower teeth and a temporomandibular joint (TMJ) of the animal, and a processing unit including routines for:

(a) locating a right or left TMJ pivot point, (b) determining planar wear surfaces for at least two teeth on the lower jaw or the upper jaw, the selected jaw, at least one of the teeth located on an ipsilateral posterior side of the selected jaw and at least another one of the teeth located on a contralateral anterior side of the selected jaw, (c) determining normal vectors, $N_1$ and $N_2$, to the wear surfaces directed towards the non-selected jaw, (d) determining a pointing vector, $P_{TMJ}$, between the pivot point and an opposite side TMJ pivot point and position vectors, $P_1$ and $P_2$, between the pivot point and the two normal vectors $N_1$ and $N_2$ and (e) determining TMJ motion give by equation (1):

$$\begin{Bmatrix} P'_{TMJx}, \\ P'_{TMJy}, \\ P'_{TMJz}, \end{Bmatrix} = \begin{bmatrix} \cos\Phi + E_{Rx}^2(1-\cos\Phi) & E_{Rx}E_{Ry}(1-\cos\Phi) + E_{Rz}\sin\Phi & E_{Rx}E_{Rz}(1-\cos\Phi) - E_{Ry}\sin\Phi \\ E_{Rx}E_{Ry}(1-\cos\Phi) - E_{Rz}\sin\Phi & \cos\Phi + E_{Ry}^2(1-\cos\Phi) & E_{Ry}E_{Rz}(1-\cos\Phi) + E_{Rx}\sin\Phi \\ E_{Rx}E_{Rz}(1-\cos\Phi) + E_{Ry}\sin\Phi & E_{Ry}E_{Rz}(1-\cos\Phi) - E_{Rx}\sin\Phi & \cos\Phi + E_{Rz}^2(1-\cos\Phi) \end{bmatrix} \begin{Bmatrix} P_{TMJx} \\ P_{TMJy} \\ P_{TMJz} \end{Bmatrix} \quad (1)$$

where $P'_{TMJx}$, $P'_{TMJy}$, and $P'_{TMJz}$ are components of an opposite TMJ trajectory vector $P'_{TMJ}$, $\Phi$ is any rotation about the TMJ pivot point, $P_{TMJx}$, $P_{TMJy}$, and $P_{TMJz}$ are components of a TMJ position vector $P_{TMJ}$, and a 3×3 rotation matrix, where in the 3×3 rotation matrix, $E_{rx}$, $E_{ry}$, and $E_{Rz}$ are component of a vector $E_R$ given by equation (2)

$$\vec{E}_R = \frac{\vec{N}_{P1} \times \vec{N}_{P2}}{|\vec{N}_{P1} \times \vec{N}_{P2}|} \quad (2)$$

where $N_{P1}$ is a vector cross product given by equation (3):

$$\vec{N}_{P1} = \vec{P}_1 \times \vec{N}_1 \quad (3)$$

where $N_2$ is a vector cross products given by equation (4):

$$\vec{N}_{P2} = \vec{P}_2 \times \vec{N}_2 \quad (4)$$

where the equation (1) predicts TMJ motion.

* * * * *